United States Patent [19]

Togawa

[11] Patent Number: 5,708,851
[45] Date of Patent: Jan. 13, 1998

[54] SYSTEM FOR MANAGING INFORMATION BY USING HYBRID CARD IN MAIN AND SUBDATA PROCESSING APPARATUSES

[75] Inventor: Tsuyoshi Togawa, Hino, Japan

[73] Assignee: Olympus Optical Company, Ltd., Tokyo, Japan

[21] Appl. No.: 992,036

[22] Filed: Dec. 17, 1992

[30] Foreign Application Priority Data

Dec. 18, 1991 [JP] Japan ..................... 3-334941

[51] Int. Cl.⁶ ............... G06F 15/42; G06F 12/14; G06F 15/30
[52] U.S. Cl. ............................ 395/872; 395/404
[58] Field of Search .................. 395/425, 275, 395/872, 282, 404; 369/32

[56] References Cited

U.S. PATENT DOCUMENTS

| | | | |
|---|---|---|---|
| 4,833,310 | 5/1989 | Shimamura et al. | 235/479 |
| 4,837,843 | 6/1989 | Owechko | 382/31 |
| 4,868,373 | 9/1989 | Opheij et al. | 235/380 |
| 4,960,982 | 10/1990 | Takahira | 235/382 |
| 5,010,237 | 4/1991 | Kawana | 235/379 |
| 5,093,862 | 3/1992 | Swartz | 380/25 |
| 5,132,947 | 7/1992 | Kameda et al. | 369/32 |
| 5,265,230 | 11/1993 | Saldanha et al. | 395/425 |
| 5,293,610 | 3/1994 | Schwarz | 395/425 |
| 5,319,765 | 6/1994 | Kimura | 395/425 |
| 5,341,291 | 8/1994 | Roizen et al. | 364/413.02 |

FOREIGN PATENT DOCUMENTS

| | | |
|---|---|---|
| 63-165957 | 7/1988 | Japan. |
| 63-165958 | 7/1988 | Japan. |
| 63-165959 | 7/1988 | Japan. |
| 63-165963 | 7/1988 | Japan. |
| 63-165964 | 7/1988 | Japan. |
| 63-167269 | 7/1988 | Japan. |

Primary Examiner—Thomas C. Lee
Assistant Examiner—Rehana Krick

[57] ABSTRACT

In a system for managing medical information by using a hybrid card having an optical stripe and an IC module, in a hospital there is provided a main data processing apparatus which can write and read data on and from the optical stripe of the hybrid card and can write and read data from the IC module, and in a patient's home there is arranged a sub data processing apparatus for reading and writing the data on and from the IC module. The patient measures blood pressure and heart rate at home, and the measured data is recorded on the IC module. In the hospital the blood pressure and heart rate stored in the IC module are read out and are used for diagnosis. As the sub data processing apparatus installed in the patient's home could not write data on the optical stripe, the apparatus can be made small in size, simple in construction and cheap in cost. Further, the important data stored in the optical stripe could not be erased or altered by the patient. The sub data processing apparatus may be formed to read limited data stored on the optical stripe.

15 Claims, 21 Drawing Sheets

FIG_1A
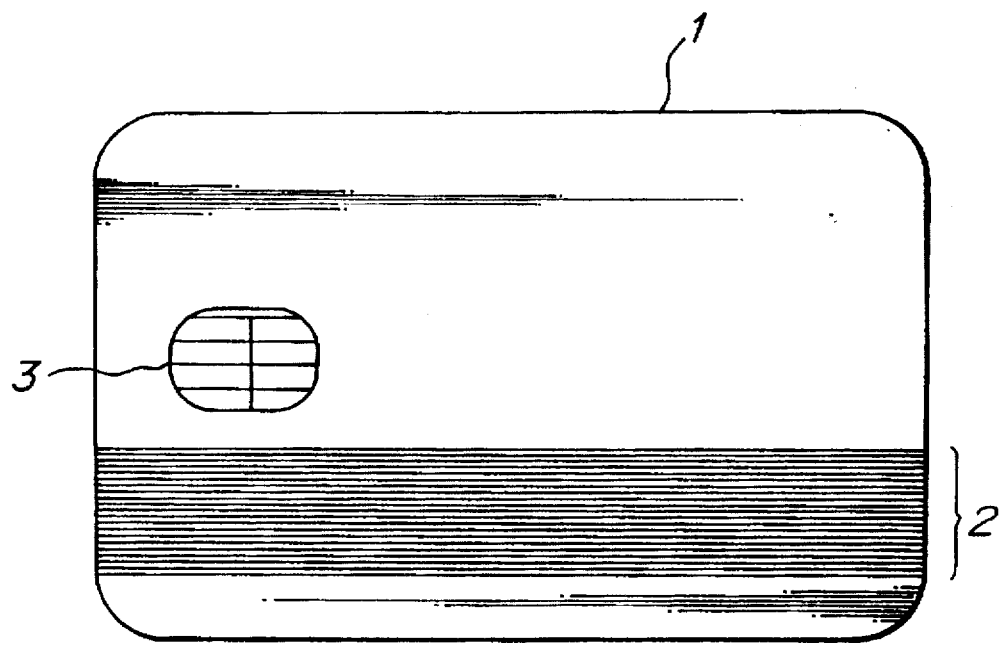
FIG_1B
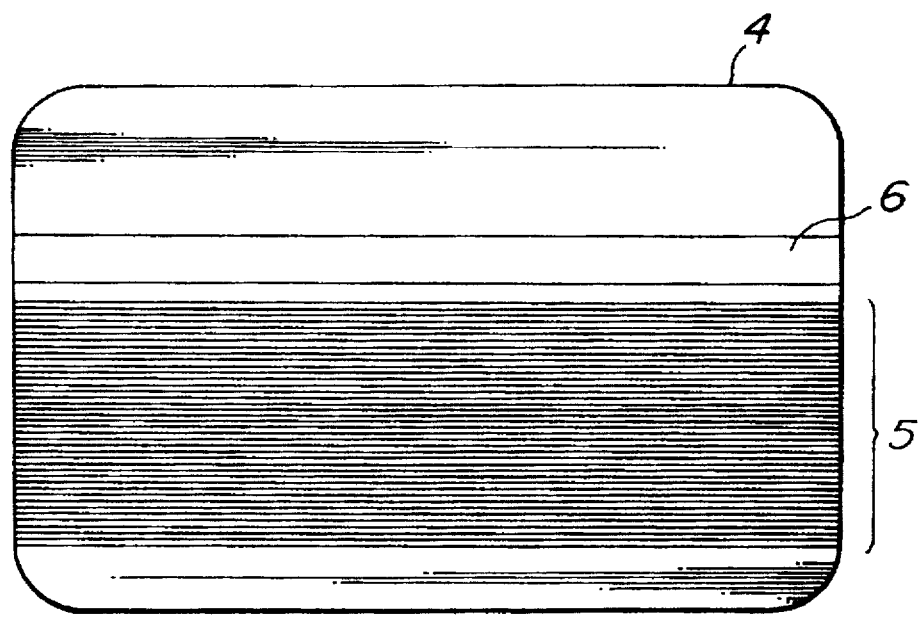

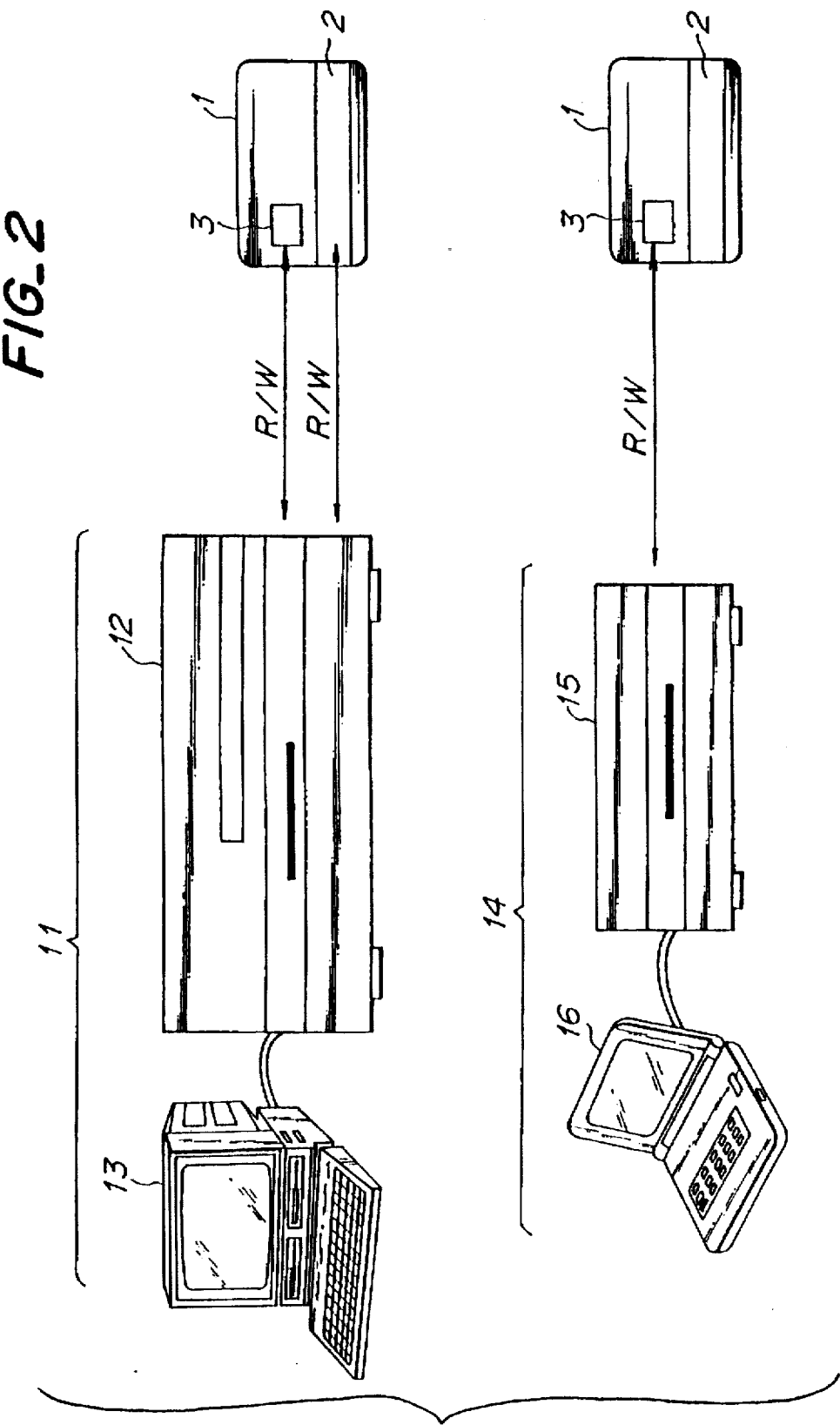

FIG_5
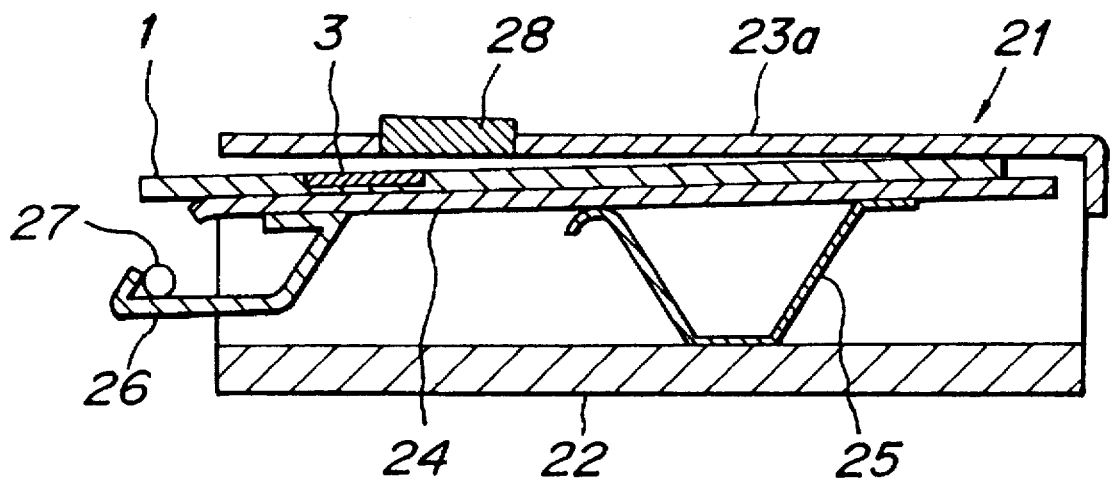
FIG_6
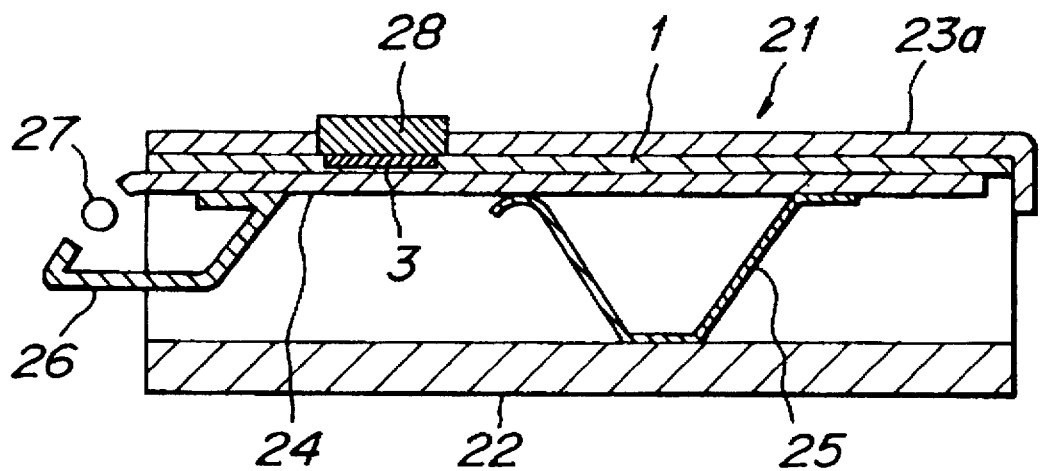

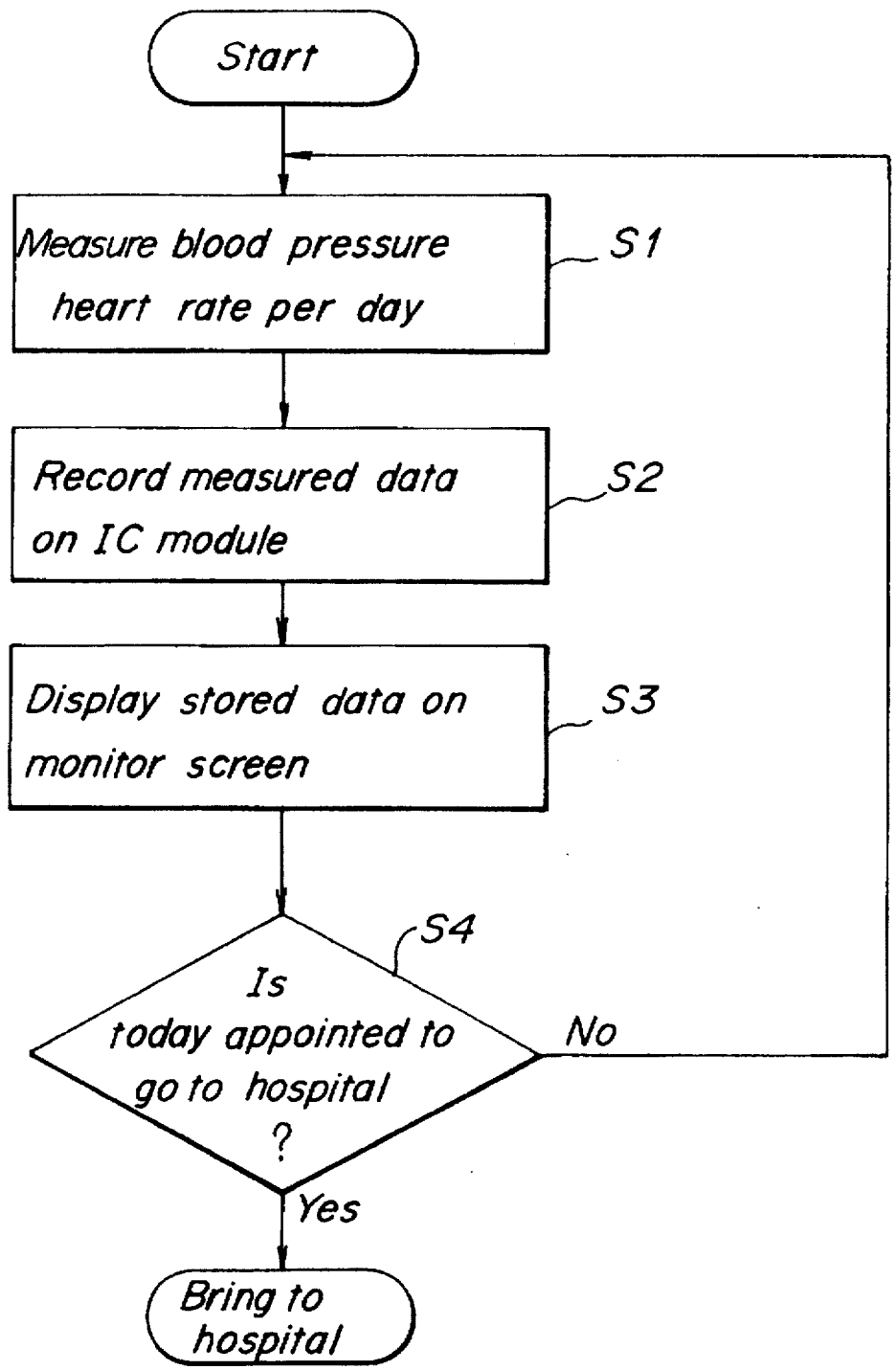

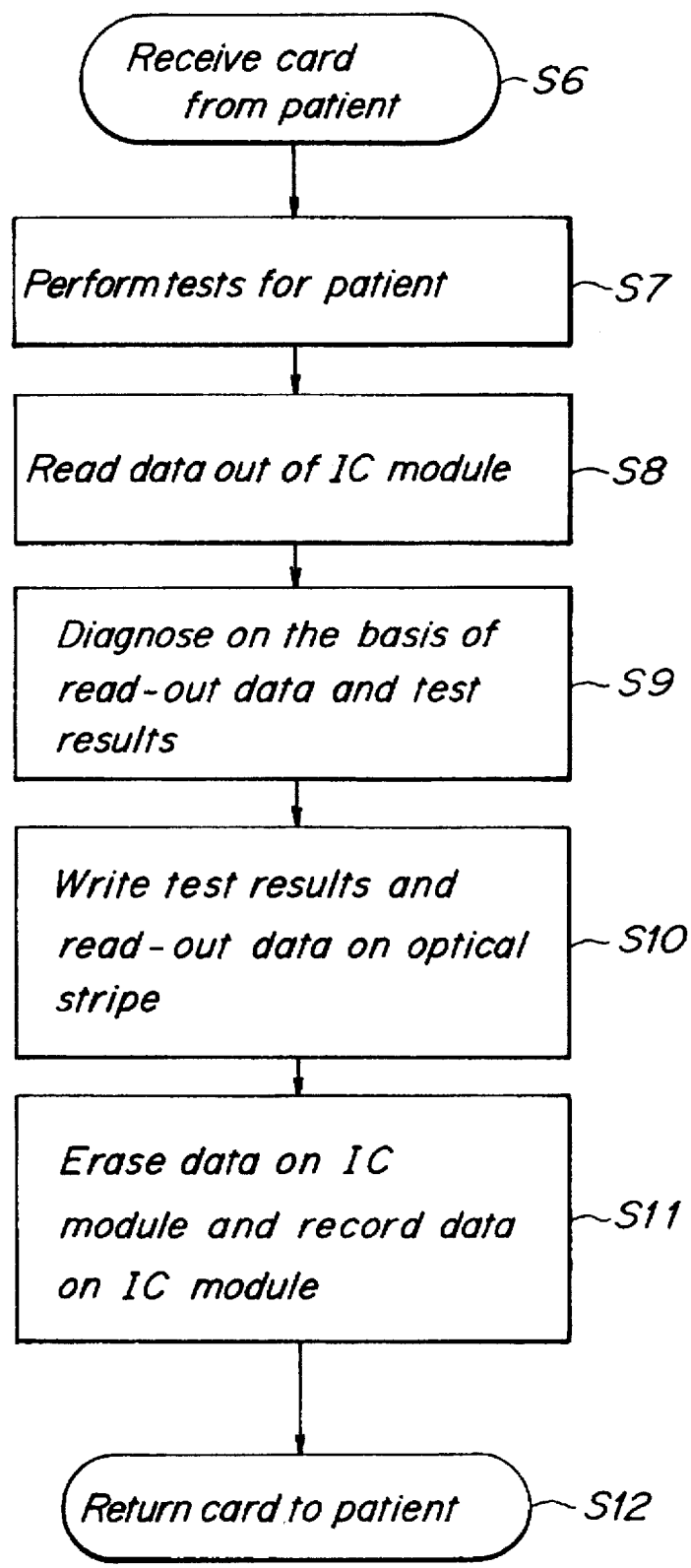
FIG_8

FIG_10A

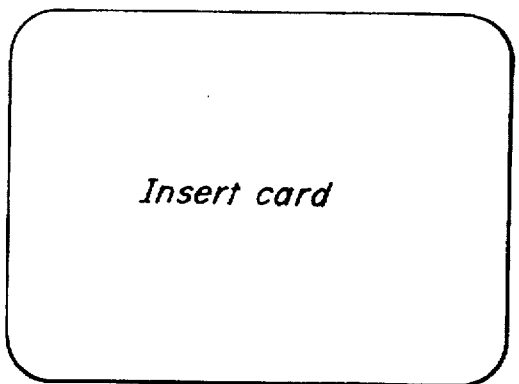

Insert card

I1

FIG_10B

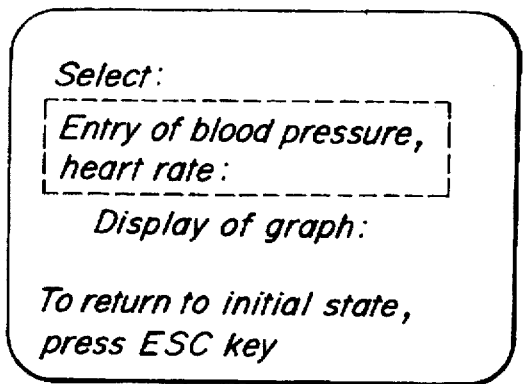

Select:
Entry of blood pressure,
heart rate:

Display of graph:

To return to initial state,
press ESC key

M1

FIG_10C

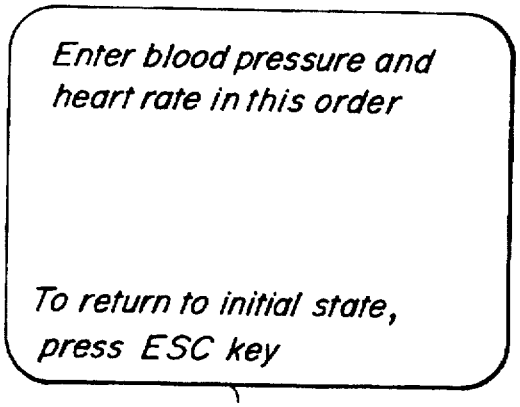

Enter blood pressure and
heart rate in this order

To return to initial state,
press ESC key

M2

FIG_10D

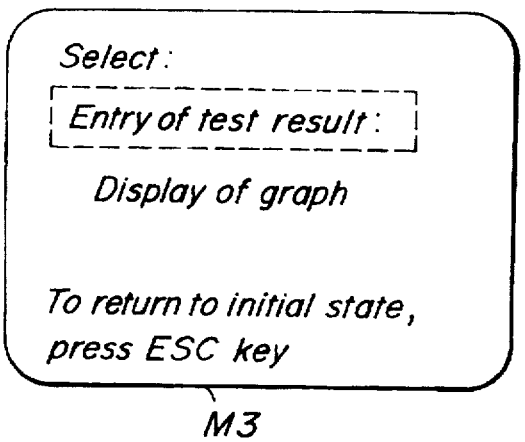

Select:
Entry of test result:

Display of graph

To return to initial state,
press ESC key

M3

FIG_10E

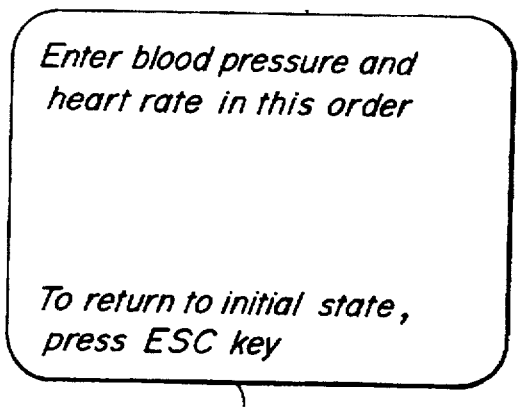

Enter blood pressure and
heart rate in this order

To return to initial state,
press ESC key

M4

FIG_10F

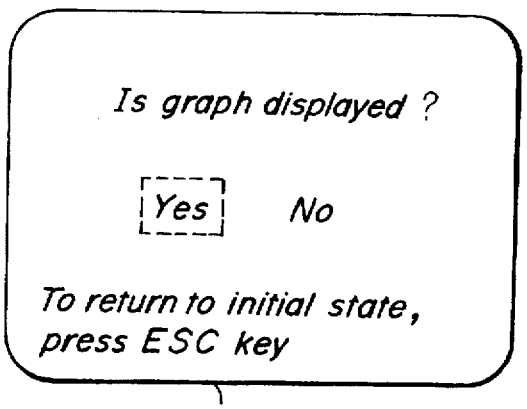

Is graph displayed?

Yes    No

To return to initial state,
press ESC key

M5

FIG_12

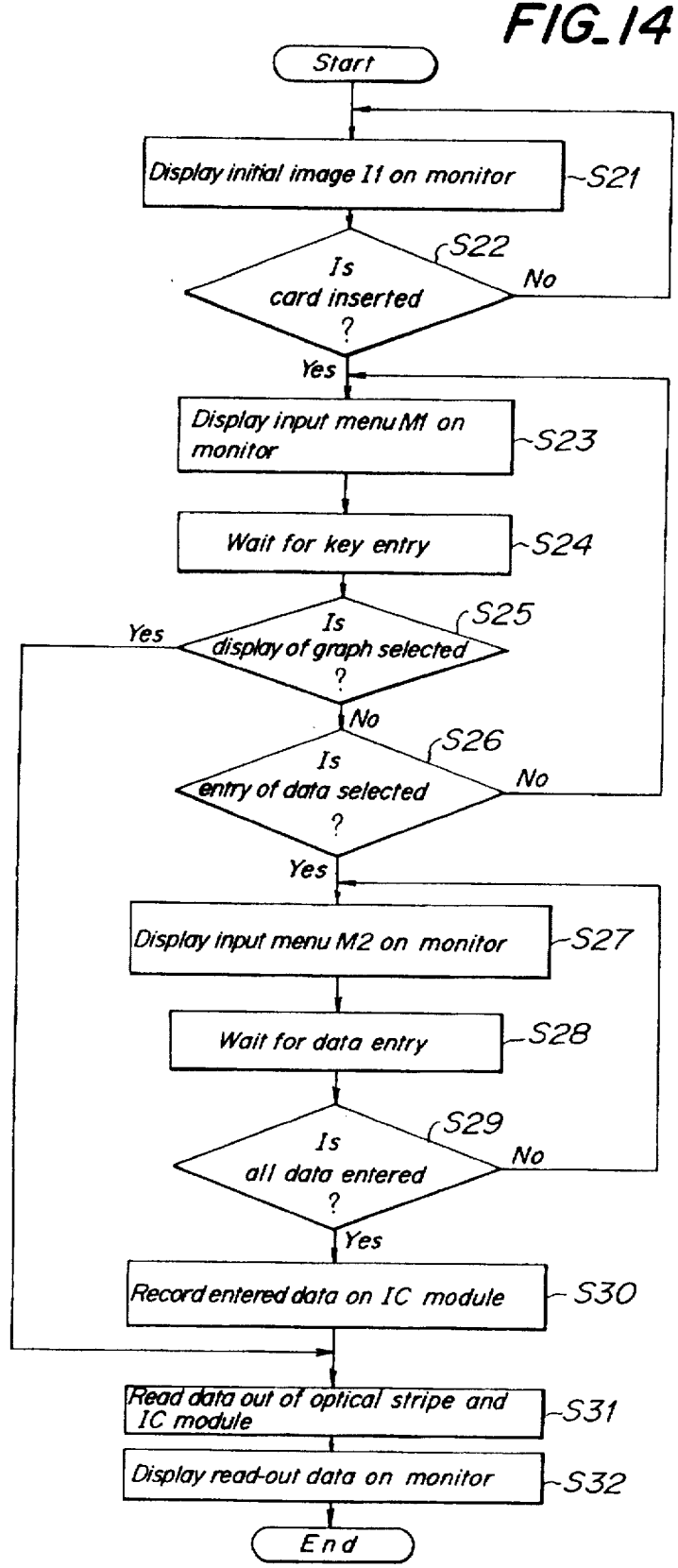
FIG_14

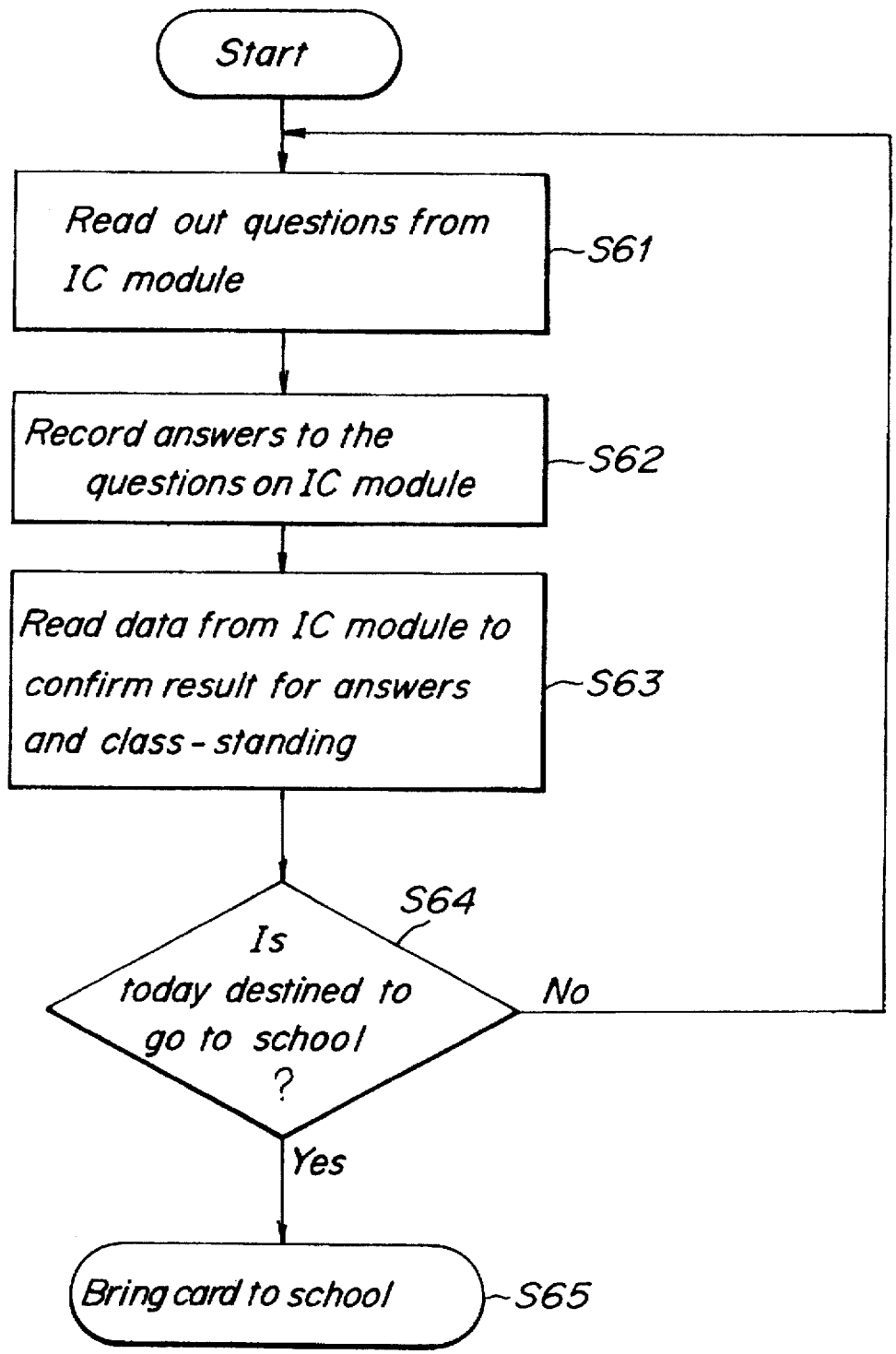
FIG_16

FIG_17
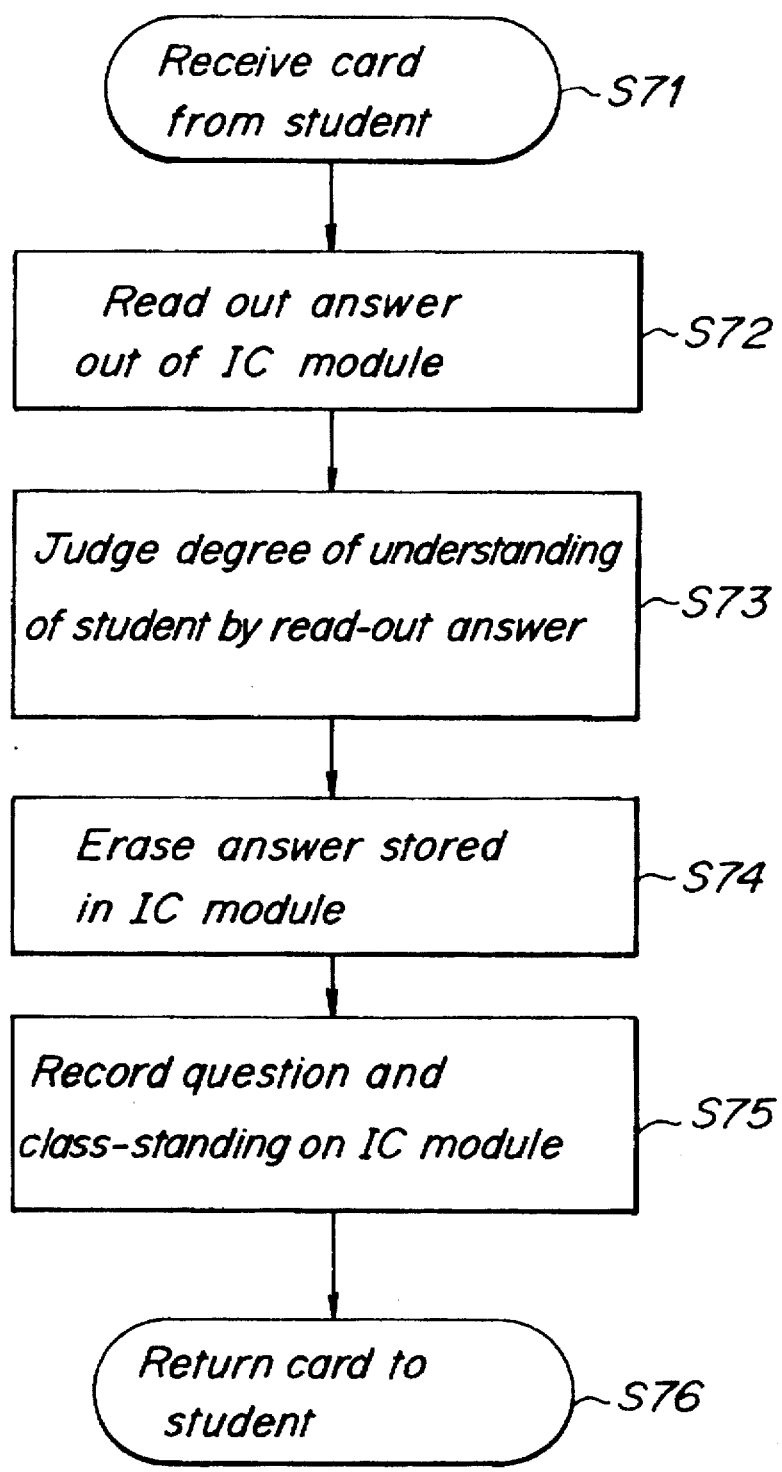

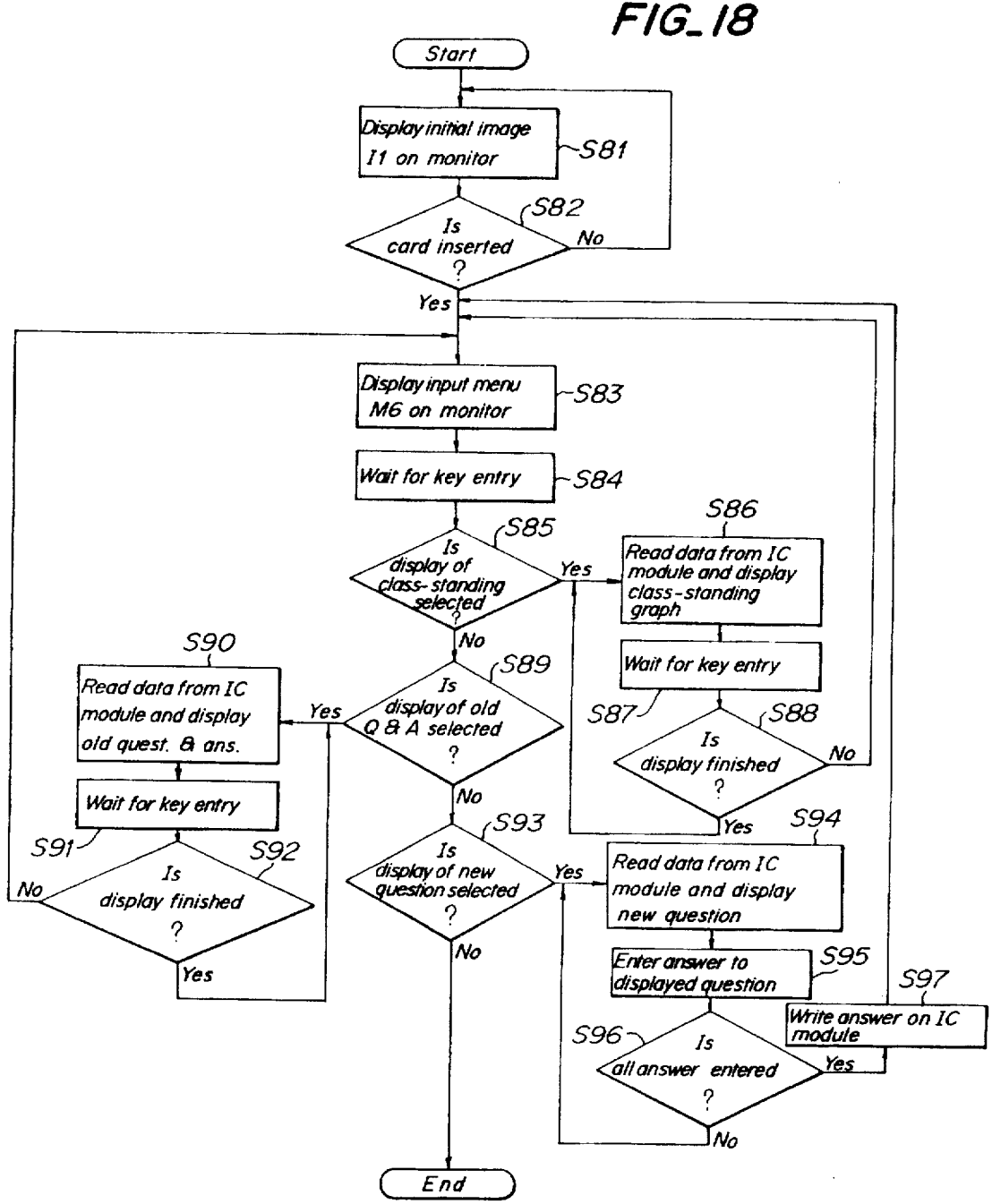

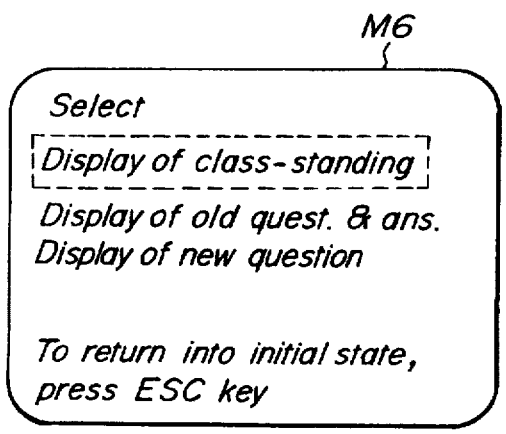
FIG_19A
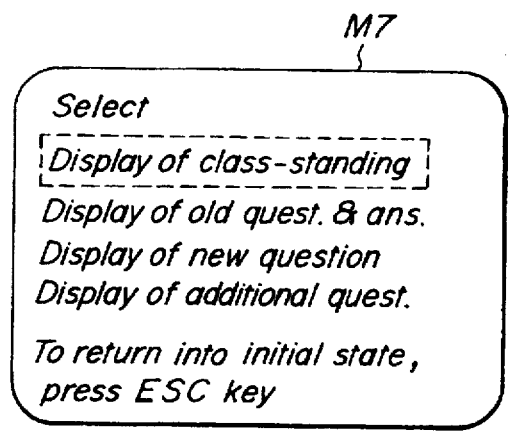
FIG_19B

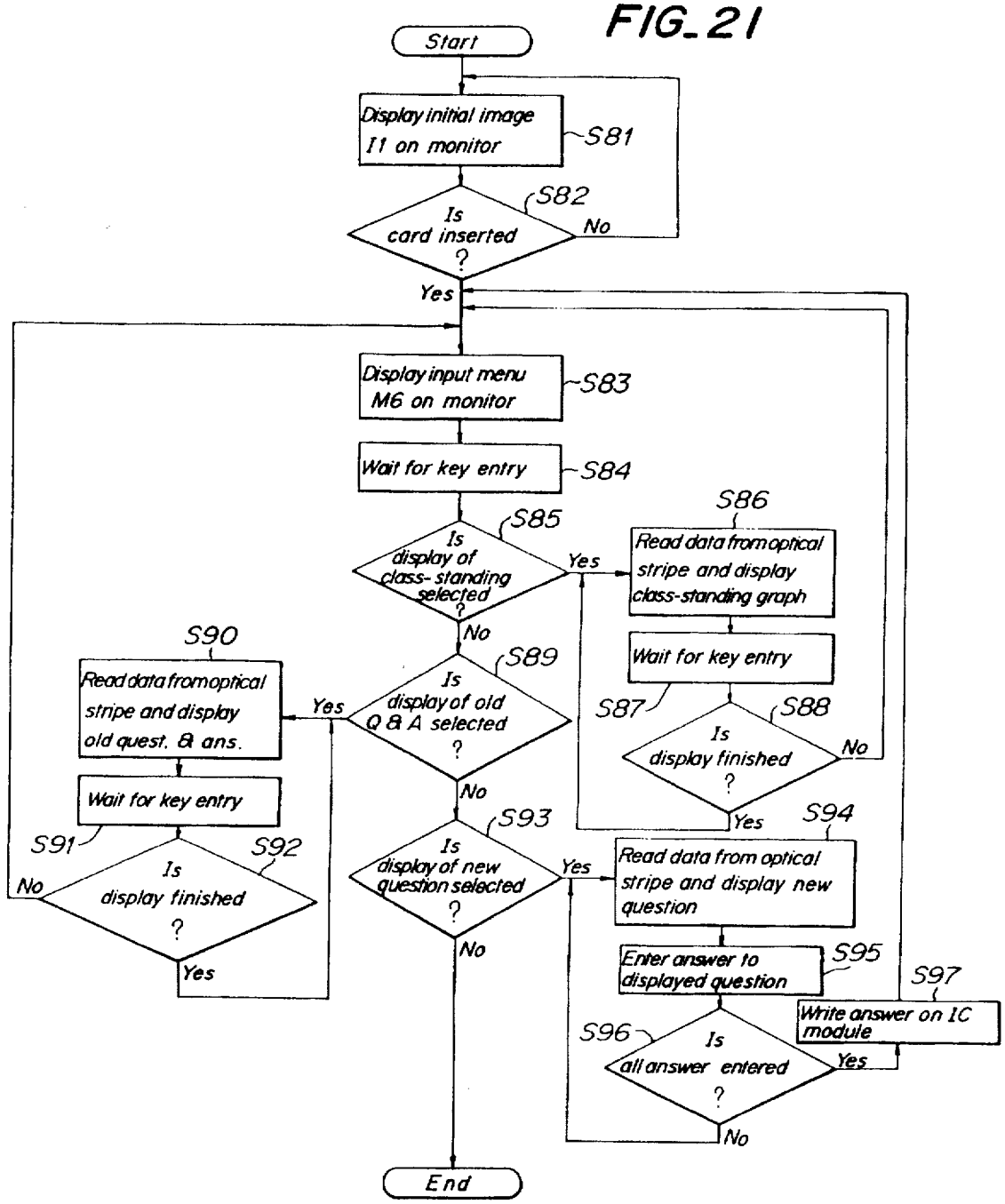
FIG_21

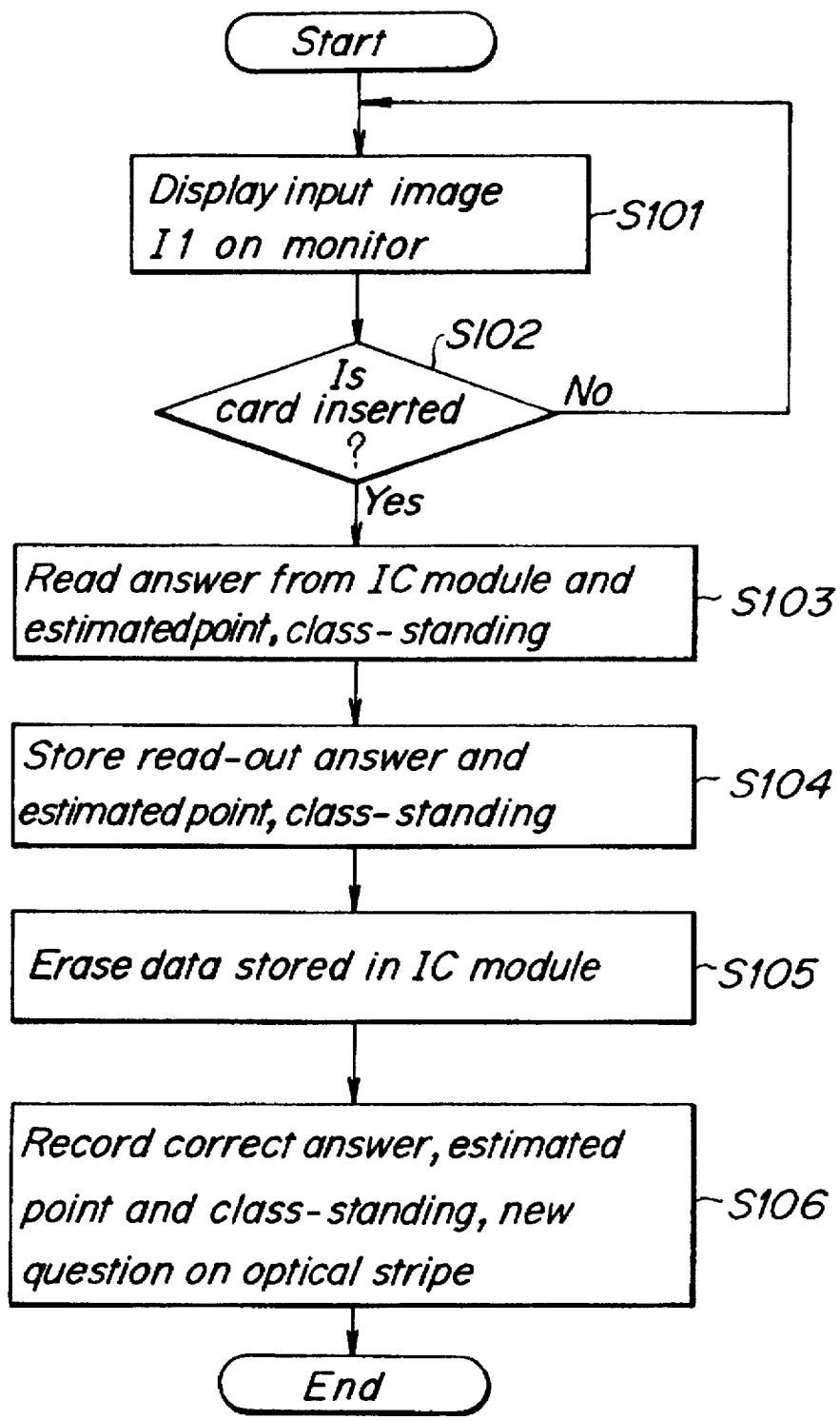
FIG_22

SYSTEM FOR MANAGING INFORMATION BY USING HYBRID CARD IN MAIN AND SUBDATA PROCESSING APPARATUSES

BACKGROUND OF THE INVENTION

1. Field of the Invention

The present invention relates to a system for managing information by using a hybrid card having first data record area of a write-once type such as an optically recordable and readable data record area and a second data record area of a rewritable type such as an electrically recordable and readable data record area and a magnetically recordable and readable data record area.

2. Description of the Related Art

An information related industry has been remarkably developed, and the amount of information to be managed has increased day by day. As record media for managing personal information, the optical card and the IC card have been developed. These cards have contradictory functions, i.e., portability and large capacity. That is to say, they can be easily carried with users and have large data storing capacity.

Particularly, the optical card has a data storing capacity over 2 megabytes. Further, the optical card is of the write-once type, so that data once recorded on the optical card could not be altered easily. Due to these superior functions of the optical cards, various applications for the optical card have been proposed. For instance, Japanese Patent Application Laid-open Publications Nos. 63-165957, 63-165958, 63-165959, 63-165963, 63-165964 and 63-167269, there are disclosed various applications for managing medical information by using the optical cards.

In these known methods of managing the personal medical information by using the optical cards, it is possible to effect various functions such as setting of standards for judgments of test data, processing of the test data, management of the test data, and display of the test data. Further, by using the optical cards it is also possible to know easily the history of data stored in the optical cards.

There has been further developed an optical/IC hybrid card in which an optically recordable and readable stripe and an electrically recordable and readable IC module are provided on the same card. In the known hybrid card, the optical stripe is utilized to store the data, and the IC module is used for managing the data stored in the optical stripe and for effecting the security of data.

In the above explained applications, the user can easily bring the card with him or her, so that in any medical organizations the personal medical data can be read out of the card, and prompt and suitable treatment can be expected even when the user is on a trip.

However, in the known method of managing information by using the hybrid card, the user could not access to the data stored in the card, and therefore the user could not effect self management for health on the basis of useful medical data stored in the card. Recently there have been developed domestic type blood pressure and heart rate measuring devices and the user can measure the blood pressure easily at home under a relaxed condition. However, the blood pressure and heart rate measured by the user can not be recorded on the card. It should be noted that the blood pressure and heart rate measured under the relaxed condition are very useful for a doctor, but the doctor could not utilize this information. In order to avoid the above mentioned drawback, one can consider to provide an apparatus for recording and reading information on and from the hybrid card in a user's home. However, this apparatus is liable to be large and expensive, because the apparatus has to be constructed to read and write the data on and from both the optical stripe and IC module. Moreover, if such an apparatus is installed in the user's home, the data stored on the hybrid card is equally accessible to the user and the doctor, and this results in another drawback in that the important data might be altered or erased.

SUMMARY OF THE INVENTION

The present invention has for its object to provide a novel and useful system for managing information by using a hybrid card, in which the above mentioned drawbacks can be mitigated and the user can record data on the hybrid card and can read the data by means of a rather simple and inexpensive apparatus, while the important data stored on the hybrid card could not be intentionally or accidentally changed or erased by a user.

According to the invention, a system for managing information by using a hybrid card having a first data record area of write-once type and a second data record area of rewritable type comprises a main data processing apparatus which comprises a first card treating means for writing and reading data on and from said first data record area and a second card treating means for writing and reading data on and from said second data record area; and a sub data processing apparatus which is arranged separately from said main data processing apparatus and comprises a card treating means for writing and reading data on and from said second data record area.

According to further aspect of the invention, a system for managing information by using a hybrid card having a first data record area of write-once type and a second data record area of rewritable type comprises a main data processing apparatus which comprises a first card treating means for writing and reading data on and from said first data record area and a second card treating means for at least reading data from said second data record area; and a sub data processing apparatus which is arranged separately from said main data processing apparatus and comprises a first card treating means for reading data from said first data record area and a second card treating means for at least writing data on said second data record area.

According to the invention, the sub data processing apparatus which is operated by a user could not write data on the first data record area of write-once type, so that the important data could not be altered or erased. Further, as it is not necessary to construct the sub data processing apparatus to write data on the first data record area, this apparatus can be made simple in construction, small in size and cheap in cost.

In a preferable embodiment of the present invention, the sub data processing apparatus is constructed such that it can read only a part of the data stored in the first data record area. Then, predetermined data can be hidden from the user to perform security functions.

BRIEF DESCRIPTION OF THE DRAWINGS

FIGS. 1A and 1B are plan views showing the hybrid cards which can be advantageously used in the information managing system according to the invention;

FIG. 2 is a view illustrating a the whole construction of a first embodiment of the system according to the invention;

FIGS. 5 and 6 are cross sections depicting the operation of the shuttle;

FIG. 7 is a flow chart representing the manner of using the hybrid card in the patient home;

FIG. 8 is a flow chart showing the manner of using the hybrid card in the hospital;

FIGS. 10A, 10B, 10C, 10D, 10E and 10F show various images displayed on the monitor of the sub data processing apparatus;

FIG. 14 is a flow chart representing the operation of the sub data processing apparatus;

FIG. 16 is a flow chart showing the manner of using the hybrid card in the student home in a third embodiment of the information managing system according to the invention;

FIG. 17 is a flow chart representing the manner of using the hybrid card in the educational facility;

FIG. 18 is a flow chart showing the operation of the sub data processing apparatus installed in the student home;

FIGS. 19A and 19B show input means displayed on the sub data processing apparatus;

FIG. 21 is a flow chart showing the operation of the sub data processing apparatus in a fourth embodiment of the information managing system according to the invention; and FIG. 22 is a flow chart illustrating the operation of the main data processing apparatus in the fourth embodiment.

DETAILED DESCRIPTION OF THE PREFERRED EMBODIMENT

Figure 3:
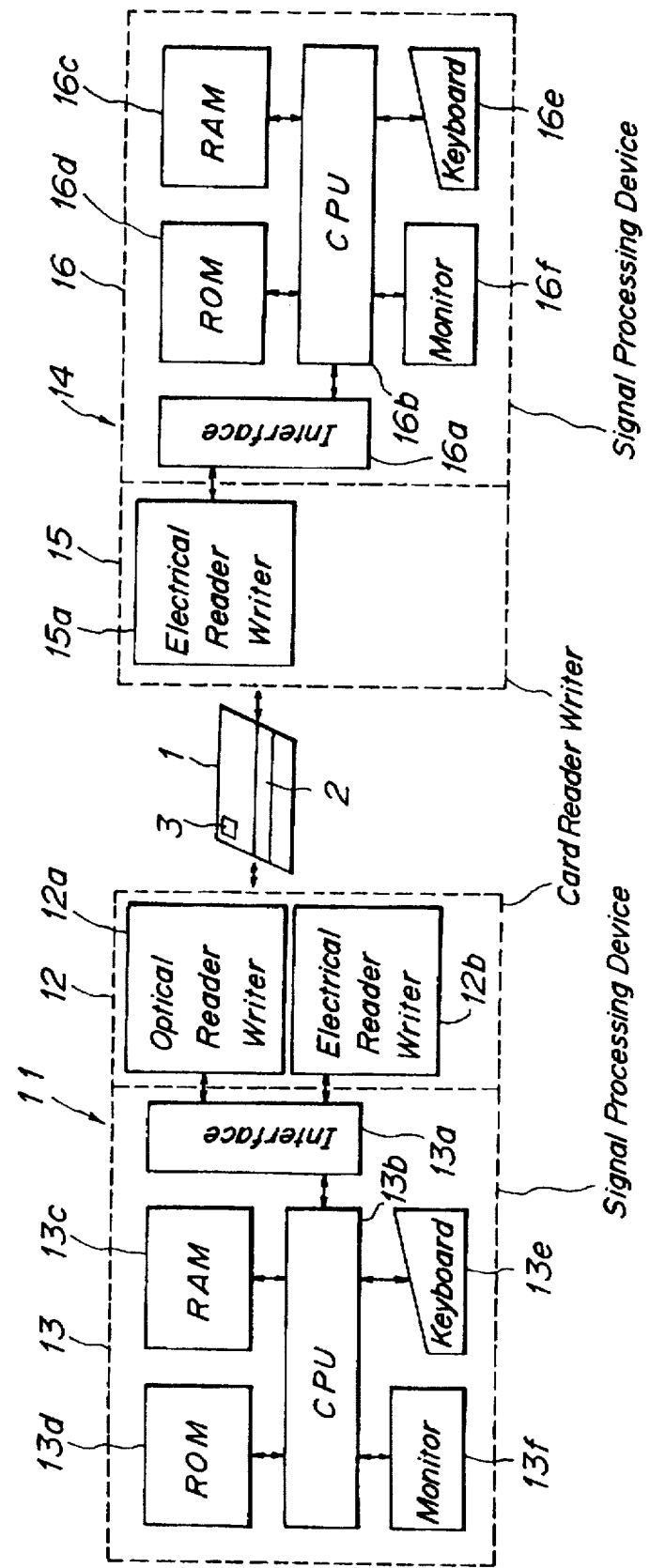
FIG. 3 is a block diagram depicting the system shown in FIG. 2.

FIGS. 1A and 1b are plan views showing two embodiments of the hybrid card which can be advantageously used in the system according to the invention. In the hybrid card 1 shown in FIG. 1A, an optical stripe 2 and IC module 3 are arranged on the card. The optical stripe 2 constitutes a data record area of write-once type, and data could not be written by erasing previously recorded data, and includes a number of tracks arranged in parallel with each other. The IC module 3 forms a data record area of rewritable type, and new data can be recorded by erasing previously recorded data. Such a hybrid card 1 is sometimes called an optical/IC card.

In a hybrid card 4 illustrated in FIG. 1B, an optical stripe 5 having a relatively large width and a magnetic tape 6 are provided. The optical stripe 5 provides the first data record area of write-once type, and the magnetic tape 6 constitutes the second data record area of rewritable type.

According to the invention, various kinds of the hybrid card may be utilized. In embodiments to be explained hereinbelow, the optical/IC card 1 illustrated in FIG. 1A is utilized.

FIG. 2 shows the whole construction of the information managing system according to the invention using the hybrid card 1. The system comprises a main data processing apparatus 11 having a card reader and writer 12 and a signal processing device 13 similar to a personal computer. The card writer and reader 12 can write data on both the optical stripe 2 and IC module 3 and can read data from both the optical stripe and IC module. The system further comprises a sub data processing apparatus 14 which is separately arranged from the main data processing apparatus 11 and which includes a card reader and writer 15 and a signal processing device 16 having small keyboard and display. The card reader and writer 15 of the sub data processing apparatus 14 can read data only from IC module 3 and can write data only on the IC module. That is to say, the card reader and writer 15 does not have to be constructed access to the optical stripe 2, so that it can be made simple in construction, small in size and cheap in cost as compared with the card reader and writer 12 of the main data processing apparatus 11. Furthermore, the signal processing device 16 of the sub data processing apparatus 14 can be made simple, small and cheap. In the medical application, the hybrid card 1 is issued for respective patients, the main data processing apparatus 11 is provided in a hospital, and the sub data processing apparatuses 14 are installed in respective patients' homes.

FIG. 3 is a block diagram illustrating the more detailed construction of the system shown in FIG. 2. The card reader and writer 12 of the main data processing apparatus 11 includes an optical reading and writing unit 12a for writing and reading data on and from the optical stripe 2 on the hybrid card 1 and an electrical reading and writing unit 12b for writing and reading data on and from the IC module 3 on the hybrid card. The signal processing device 13 of the main data processing apparatus 11 comprises interface 13a, central processing unit (CPU) 13b, random access memory (RAM) 13c, read only memory (ROM) 13d, keyboard 13e and monitor 13f.

The card reader and writer 15 of the sub data processing apparatus 14 comprises an electrical reading and writing unit 15a for reading and writing data from and on the IC module 3 of the hybrid card 1. The signal processing device 16 of the sub data processing apparatus 14 comprises interface 16a, central processing unit (CPU) 16b, random access memory (RAM) 16c, read only memory (ROM) 16d, keyboard 16e and monitor 16f. As stated above the signal processing devices 13 and 16 may be constructed similarly to an ordinary personal computer, so that a detailed explanation thereof may be dispensed with.

Figure 4:
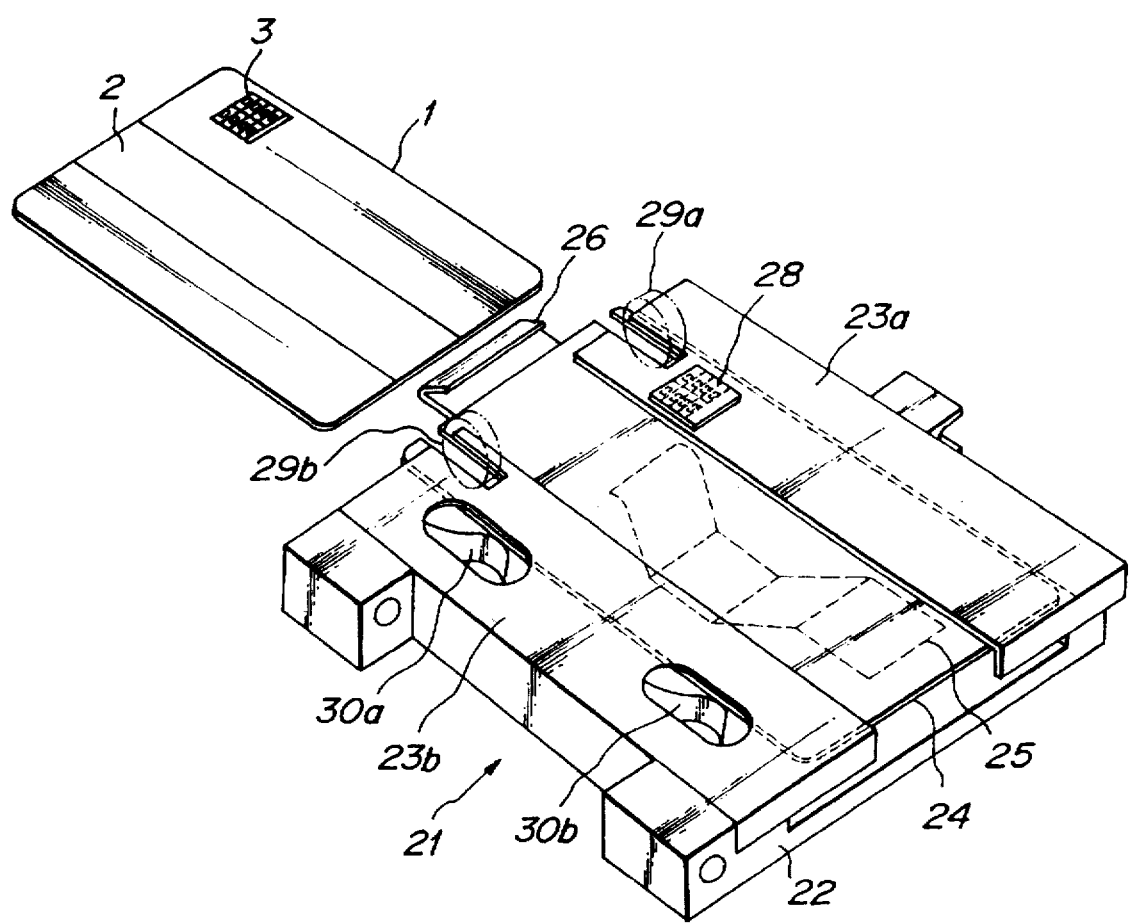
FIG. 4 is a perspective view illustrating the construction of the shuttle of the hybrid card reader and writer.

FIGS. 4, 5 and 6 illustrate the detailed construction of a part of an embodiment of the card reader and writer 12 of the main data processing apparatus 11. In optical card readers and writers, it is common practice to place the optical card on a shuttle, and the shuttle is moved reciprocally with respect to an optical head. Also in the present embodiment, the hybrid card 1 is placed on the shuttle, and the shuttle is moved with respect to the optical head in order to write and read the data on and from the optical stripe 2 of hybrid card 1. A shuttle 21 comprises a frame 22 to which a pair of card guide plates 23a and 23b are secured. These plates 23a and 23b are separated from each other by a distance which is slightly larger than a width of the optical stripe 2 so that the optical stripe is not covered with the plates when the hybrid card 1 is place on the shuttle 21. Below the card guide plates 23a and 23b there is arranged a card pushing plate 24 which is secured to a bottom of the frame 22 by means of a V-shaped leaf spring 25. To a lower surface of the card pushing plate 24 there is further secured one end of a lever 26, the other end of which is protruded from the frame 21. The card reader and writer 12 further comprises an operating rod 27 which is engageable with a bent tip of the lever 26. As shown in FIGS. 5 and 6, the operating rod 27 is moved up and down. In the card guide plate 23a there is provided a contact member 28 which is mechanically and electrically brought into contact with the contacts of the IC module 3 when the hybrid card 1 is fully inserted into the shuttle 21 as illustrated in FIG. 6. In the present embodiment, the IC module 3 of hybrid card 1 is connected to the signal processing device via the contact member 28, while the hybrid card is placed on the shuttle 21. Therefore, it is possible to always access the optical stripe 2 and IC module 3.

FIG. 5 shows a condition in which the hybrid card 1 is inserted into the shuttle 21 with the aid of card feeding means. The card feeding means includes a pair of rollers 29a and 29b shown in FIG. 4. During this condition, the operating rod 27 is in a lower position, and there is formed a sufficient space between the card guide plates 23a, 23b and the card pushing plate 24, so that the hybrid card 1 can be smoothly inserted into the shuttle 21. FIG. 6 illustrate a condition in which the hybrid card 1 has been fully inserted into the shuttle 21. In this condition, the operating rod 27 is in an upper position, so that the hybrid card 1 is urged against the card guide plates 23a, 23b by means of the resilient force of the spring 25. Further, as shown in FIG. 4, the hybrid card 1 is urged against an inner side wall of the frame 22 by means of a pair of leaf springs 30a and 30b. In this manner the hybrid card 1 can be accurately inserted into a given position within the shuttle 21.

Now the manner using the hybrid card 1 by the main and sub data processing apparatuses 11 and 14 will be explained in detail. In the present embodiment, the hybrid card is used to store the medical information such as patient's personal data, results of various measurements and tests and histories of medical treatments.

As explained above, the main data processing apparatus 11 is installed in a hospital, and the sub data processing apparatus 14 is arranged in a patient's home. The main data processing apparatus 11 can write and read data on and from both the optical stripe 2 and IC module 3 of hybrid card 1, but the sub data processing apparatus 14 can only write and read the data on and from the IC module 3.

Initially, the hospital issues a hybrid card 1 for a patient and personal data of the patient such as patient name, birthday, sex, blood type and special characteristics of the patient is written on the optical stripe 2. The patient is allowed to bring the hybrid card 1 with him or her, so that the patient can record data such as blood pressure and heart rate measured at the patient's home onto the IC module 3 of the hybrid card 1 by using the sub data processing apparatus 14.

FIG. 7 is a flow chart showing the manner of using the hybrid card 1 in the patient home. The patient measures the blood pressure and heart rate every day (step S1). To this end, there has been developed a rather simple and cheap device for measuring the blood pressure and heart rate at home. Then, in a step S2, the measured blood pressure and heart rate are recorded on the IC module 3 of hybrid card 1 by means of the sub data processing apparatus 14. After the measured data has been recorded on the IC module 3, the data is read out of the IC module and is displayed on the monitor 16f in order to check the stored data (step S3). The above explained steps are repeated until the patient goes to the hospital (step S4). The patient brings the hybrid card 1 to the hospital on an appointed day (step S5).

FIG. 8 is a flow chart representing the manner of using the hybrid card 1 in the hospital. In a step S6, the hybrid card 1 is received from the patient, and one or more necessary tests are performed for the patient to derive test results (step S7). Then, the data recorded on the IC module 3 of the hybrid card 1 is read out by means of the main data processing apparatus 11 (step S8). Now a doctor can effect the diagnosis on the basis of the thus read out data and the test results (step S9). Next the test results are recorded on the optical stripe 2 together with data read out of the IC module 3 (step S10). During this step S10, it is also possible to record additional data such as special comments or diagnosis on the optical stripe 2. Next the data recorded on the IC module 3 is erased (step S11). Also in this case, any comments which are useful for the patient may be recorded on the IC module 3. Finally, the hybrid card 1 is returned to the patient before the patient leaves the hospital.

Figure 9:
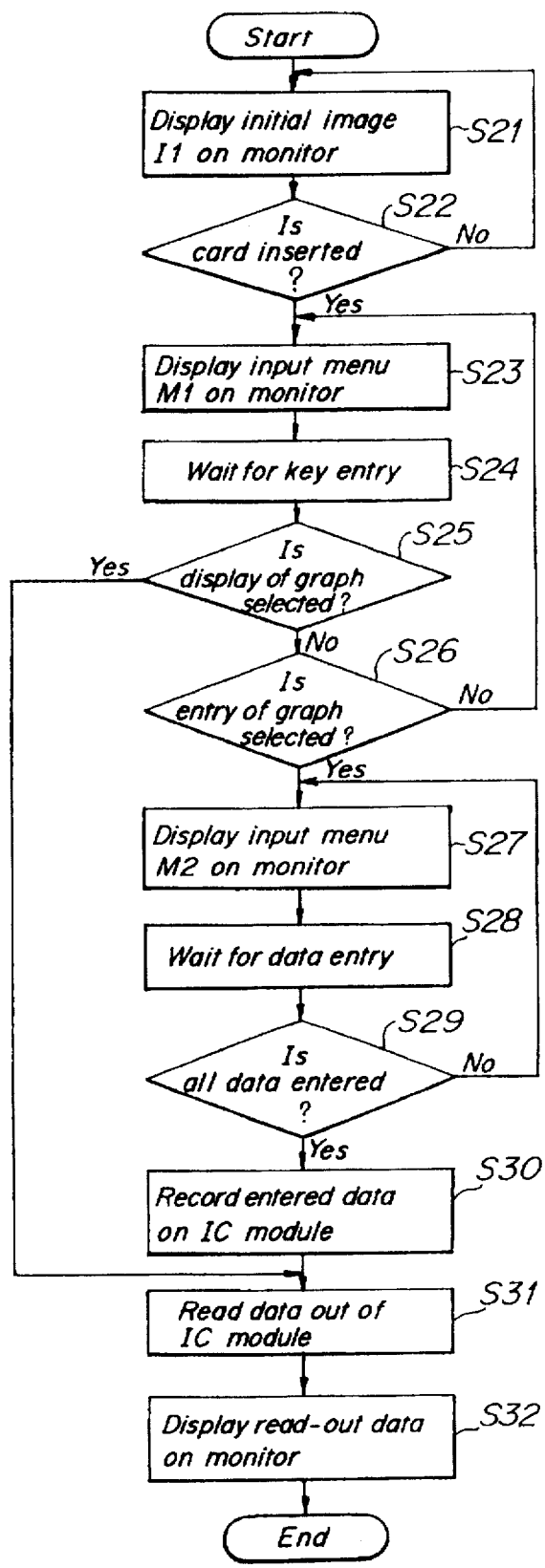
FIG. 9 is a flow chart illustrating the operation of the sub data processing apparatus.

FIG. 9 is a flow chart representing the operation of the sub data processing apparatus 14 provided in the patient home. When a power switch of the sub data processing apparatus 11 is made on, an initial image I1 shown in FIG. 10A is displayed on the monitor 15f in FIG. 3 (step S21). The the apparatus is in a condition for detecting the insertion of the hybrid card 1. When it is detected that the hybrid card 1 is inserted into the sub data processing apparatus 14, then an input menu M1 illustrated in FIG. 10B is displayed on the monitor (step S23), and the apparatus is in a condition for awaiting the key entry (step S24). In a next step S25, the apparatus is checked to see whether "Display of Graph" is selected or not. If the "Display of Graph" is not selected, then the apparatus is checked to see whether "Entry of Blood Pressure and Heart Rate" is selected or not (step S26). If "Entry of Blood Pressure and Heart Rate" is selected, an input menu M2 depicted in FIG. 10C is displayed on the monitor (step S27), and then the apparatus is in a condition for awaiting the data entry (step S28). The sub data processing apparatus 14 is checked to see whether all the data, i.e. the blood pressure and heart rate, has been entered or not (step S29). After it is confirmed that the blood pressure and heart rate have been entered, they are recorded on the IC module 3 of hybrid card 1 (step S30). Next, the recorded data is read out of the IC module (step S31), and then the thus read out data is displayed on the monitor (step S32). When in the step S25, if "Display of Graph" is selected, then the data stored in the IC module 3 of the hybrid card 1 is read out, and the read out data is processed by the signal processing device 15 of the sub data processing apparatus 14 to derive an image signal representing graphs of the blood pressure and heart rate. Then, in the step S32, the graphs of the blood pressure and heart rate are displayed on the monitor.

Figure 11:
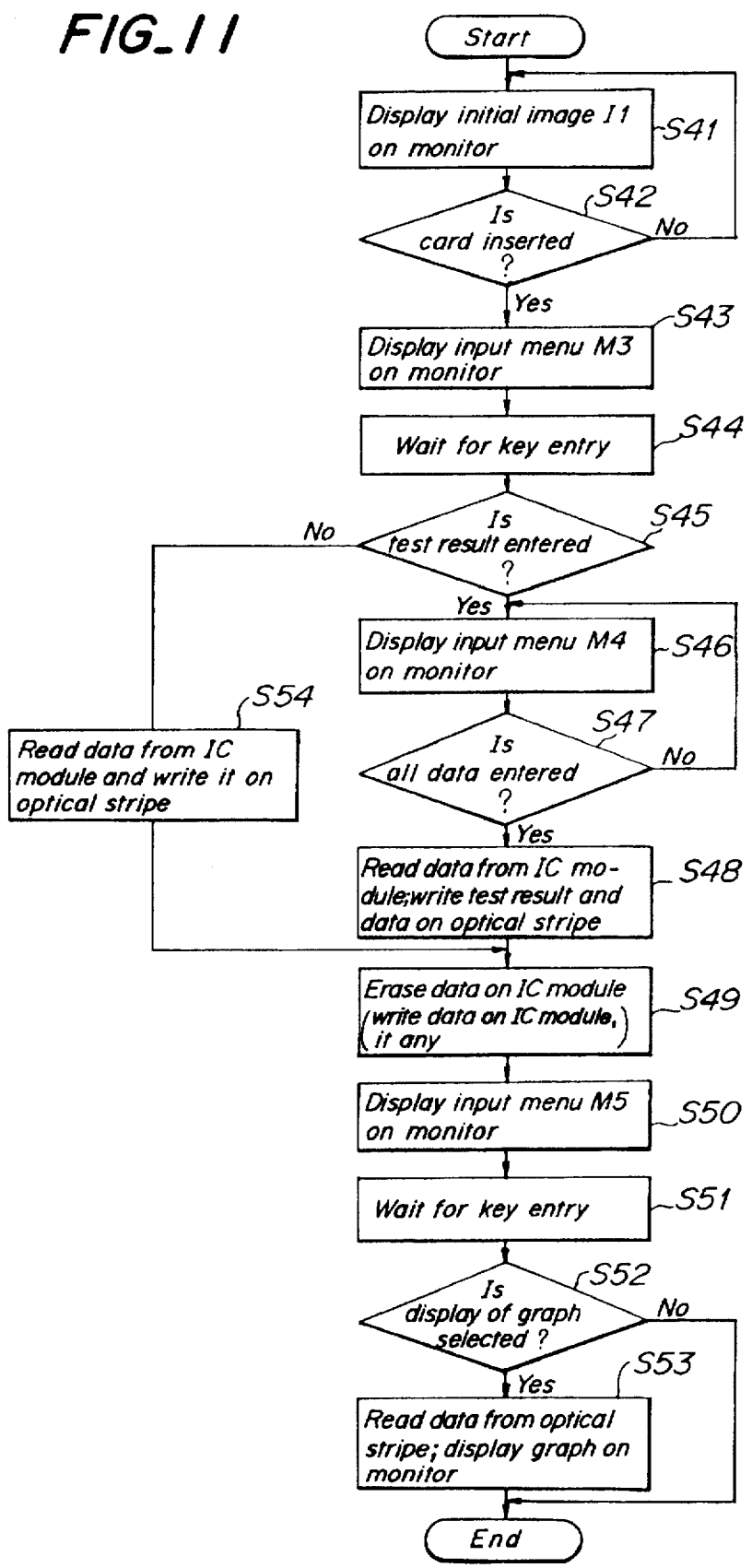
FIG. 11 is a flow chart representing the operation of the main data processing apparatus in the hospital.

FIG. 11 is a flow chart showing the operation of the main data processing apparatus 11 installed in the hospital. Upon operating a power switch, at first the initial image I1 shown in FIG. 10A is displayed on the monitor 13f of the signal processing device 13 of main data processing apparatus 11 (step S41). Then, the main data processing apparatus 11 is in a condition for checking to see whether the hybrid card 1 is inserted into the shuttle or not (step S42). Next, in a step S43, an input menu M3 illustrated in FIG. 10D is displayed on the monitor, and the apparatus is in a condition for waiting for the key entry (step S44). If "Entry of Test Result" is selected in a step S45, an input menu M4 illustrated in FIG. 10E is displayed on the monitor 13f (step S46). Then, the blood pressure, heart rate and test results can be entered in this order. When it is confirmed in a step S47 that all the data has been entered into the main data processing apparatus 11, the data stored in the IC module 3 of the hybrid card 1 is read out by the electrical reading and and writing unit 12b shown in FIG. 3 (step S48). Also in this step S48, the blood pressure and heart rate read out of the IC module 3 is recorded on the optical stripe 3 together with the test result.

Next, in a step S49, the data recorded on the IC module 3 of the hybrid card 1 is erased and comments are recorded on the IC module, if any. Then, an input menu M5 shown in FIG. 10F is displayed on the monitor in a step S50, and after that the apparatus is in a condition for waiting for the key entry (step S51). If it is confirmed that "Display of Graph" is selected (step S51), the data recorded on the optical stripe 2 of the hybrid card 1 is read out, and the read out data is processed by the signal processing device 13 of the main data processing apparatus 11 to derive an image signal representing graphs of blood pressure, heart rate and so on, and the graphs are displayed on the monitor in a step S53.

If "Display of Test Result" is selected in the step S45, then the data stored in the IC module 3 is read out, and the thus read out data is written on the optical stripe 3 in a step S54. Then, the step S54 is followed by step S49, and the data recorded on the IC module 3 is erased.

In the embodiment so far explained, the blood pressure and heart rate measured by the patient at home can be recorded on the IC module 3 of the hybrid card 1, so that the doctor can effect much more accurate diagnosis by taking into consideration such useful data. Further, as the sub data processing apparatus 14 provided in the patient home is sufficient to record the data measured by the patient's on the IC module 3 of the hybrid card 1, the apparatus can be made simple in construction, small in size and cheap in cost.

In the above embodiment, the main data processing apparatus 11 provided in the hospital comprises the electrical reading and writing unit 12b which can record the data on the IC module 3 of the hybrid card 1 and also write the data on the IC module. However, according to the invention, this electrical reading and writing unit may be replaced by an electrical reading unit which can read the data out of the IC module, but can not record the data on the IC module.

Figure 12:
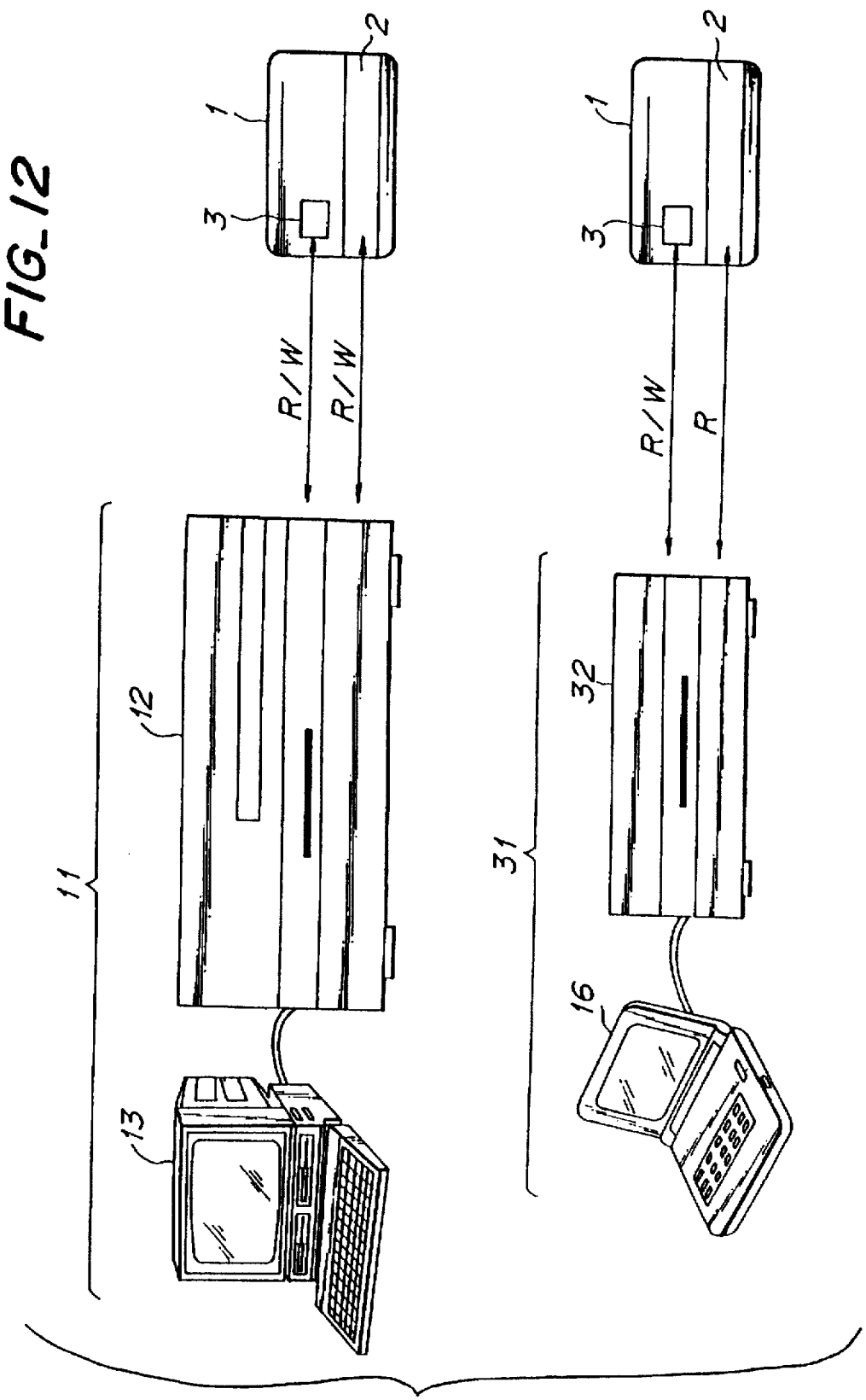
FIG. 12 shows the whole system of the second embodiment according to the invention.
Figure 13:
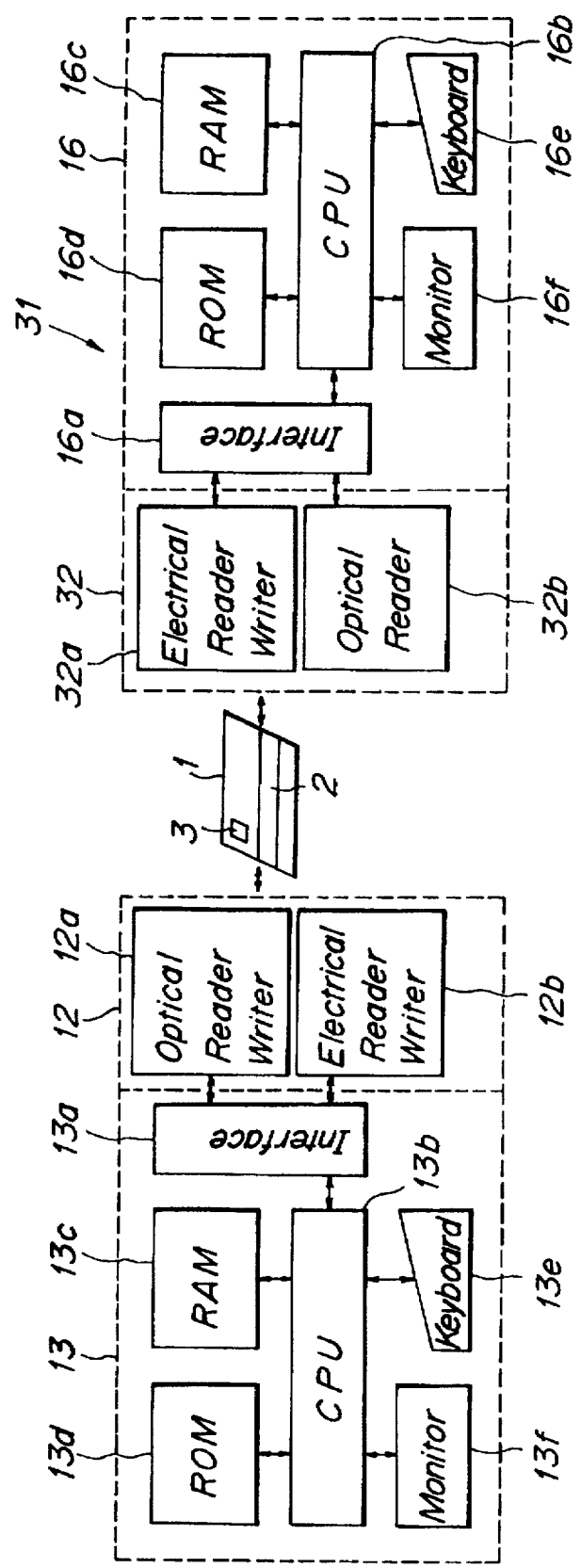
FIG. 13 is a block diagram illustrating the construction, of the system shown in FIG. 12.

FIG. 12 shows the whole construction of a second embodiment of the system according to the invention, and FIG. 13 is a block diagram illustrating the more detailed construction of the main and sub data processing apparatuses. In this second embodiment, portions similar to those of the above explained first embodiment are denoted by the same reference numerals, and their related explanation is omitted. The main data processing apparatus 11 provided in the hospital has entirely the same construction as that of the first embodiment and can write and read the data on and from both the optical stripe 2 and IC module 3 of hybrid card 1. However, the construction of a sub data processing apparatus 31 installed in a patient's home is slightly different from that of the previous embodiment. In the present embodiment, the sub data processing apparatus 31 comprises a card reader and writer 32 including, in addition to an electrical reading and writing unit 32a, an optical reading unit 32b which can read the data stored in the optical stripe 2 of hybrid card 1. The remaining construction of the sub data processing apparatus 31 of the present embodiment is same as that of the first embodiment.

FIG. 14 is a flow chart representing the operation of the sub data processing apparatus 31 provided in the patient's home. The operation of the sub data processing apparatus of the present embodiment is substantially the same as that of the first embodiment, so that its explanation is dispensed with. However, in the present embodiment, in the step S31, not only the data recorded on the IC module 3 of hybrid card 1, but also the data recorded on the optical stripe 2 are read out, and in the step S32 the thus read out data is processed to display the graphs on the monitor.

The operation of the main data processing apparatus 11 installed in the hospital of the present embodiment is entirely the same as that of the previous embodiment, so that the operation may be easily understood with reference to the flow chart illustrated in FIG. 11.

In the second embodiment, the sub data processing apparatus 31 provided in the patient's home can read the data not only from the IC module 3, but also from the optical stripe 2, but can not write data on the optical stripe, so that any undesired change or damage of the important data stored on the optical stripe does not occur. However, in some applications it is not desired or necessary to allow the patient to read all the data stored on the optical stripe 2. According to the invention, the optical reading unit 32b of the sub data processing apparatus 31 may be constructed such that only a limited portion of the data stored on the optical stripe can be read out. This security function may be performed by various methods.

Figure 15A:
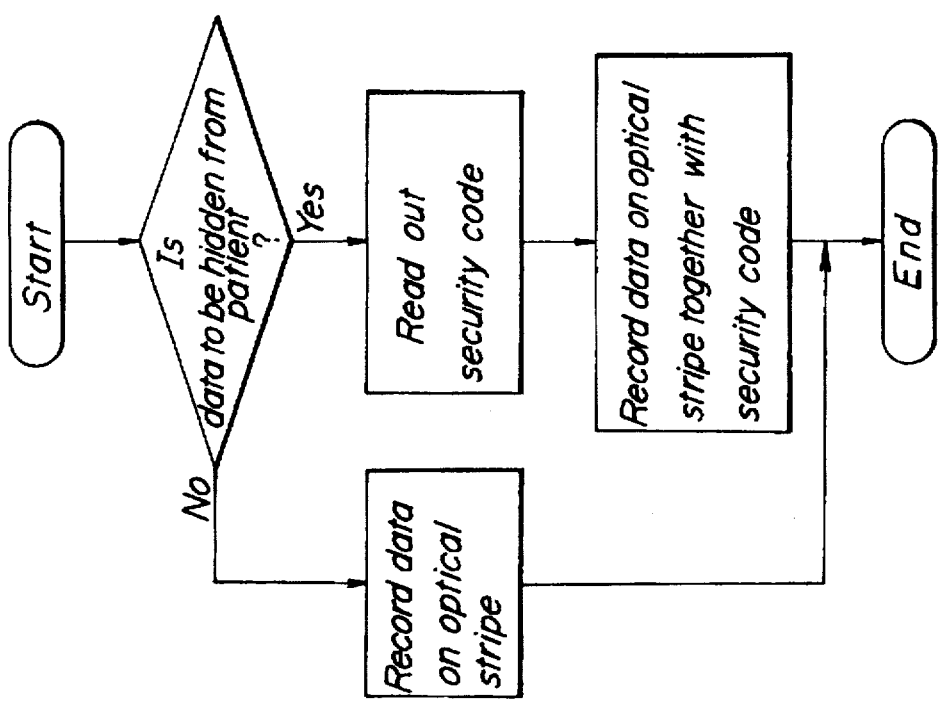
FIGS. 15A and 15B are flow charts for performing the security function.
Figure 15B:
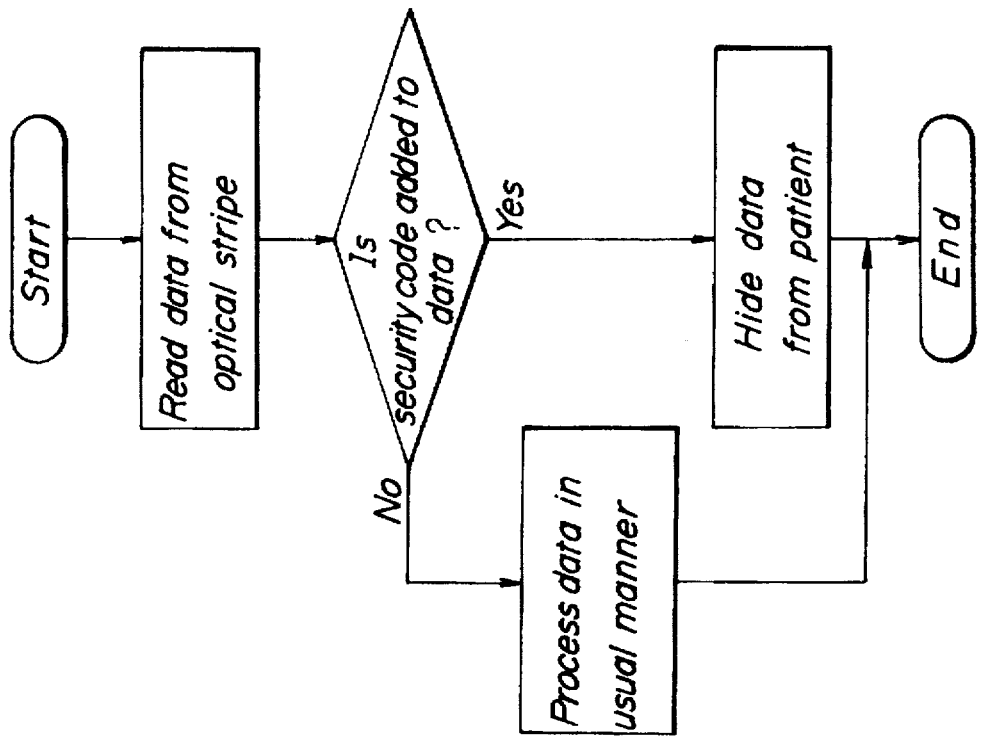

FIGS. 15A and 15B are flow charts showing the operation of an embodiment of the method for performing the above mentioned security function. FIG. 15A shows the operation at the hospital. When data is to be written on the optical stripe 2 of hybrid card 1 by using the main data processing apparatus 11, it is checked whether the relevant data has to be hidden from the patient or not. If the data do not have to be hidden from the patient, the data is written in a given sector of the optical stripe 3 in a usual manner. However, if the data has to be hidden from the patient, a predetermined security code is read out of the ROM 13d in the signal processing device 13. Then the data is written in a given sector in the optical stripe 2 of hybrid card 1 together with the security code. FIG. 15B illustrates the operation at the patient's home. When the optical stripe 2 of hybrid card 1 is read by means of the sub data processing apparatus 31, at first all the data is read out of the optical stripe together with the security code, if it is recorded. Next it is checked whether the security code is added or not for all data recorded on respective sectors. If the security code is added to data, this data is judged to be hidden from the patient, and the read out data is not displayed on the monitor 16f. If the security code is not detected, the read out data is processed in a usual manner. It should be noted that instead of the security code use may be made of a predetermined flag in a sector. When the data is to be hidden from the patient, this flag is set. In the sub data processing apparatus 31, if it is confirmed that the relevant flag is set, the relevant data is judged to be hidden from the patient and is not displayed.

In the first and second embodiments, the system is used for processing the medical data. According to the invention, the system may be applied to any other applications. In the following embodiments, the system is used for the educational application.

FIGS. 16 and 17 are flow charts showing the manner of using the hybrid card when the system shown in FIGS. 2 and 3 is applied to education. In this application, the main data processing apparatus 11 is provided in an educational facility such as a school, preparatory or fitting school and private school, and the sub data processing apparatus 14 is installed in a student's home. As shown in FIG. 16, in the student's home, the student reads out data stored in the IC module 3 of hybrid card 1 (step S61). Typically this data contains homework for the student. After solving questions in the homework, answers are recorded on the IC module by suitably operating the keyboard 16e of the signal processing device 16 of the sub data processing apparatus 14 shown in FIG. 3 (step S62). On the IC module 3 of hybrid card 1, there is also stored data such as results of the student's answers to previous questions and class-standing of the relevant student. In a step S63, this data is read out of the IC module and is displayed on the monitor 16f. The operation in the educational facility is illustrated in FIG. 17. At first the hybrid card 1 is received from the student (step S71), and then the student's answers stored in the IC module 3 are read out (step S72). Next, the degree of understanding of the student is judged on the basis of the thus read out answers to derive the order of place of the student, i.e., class-standing (step S73). After that, the answers stored in the IC module 3 are erased (step S74). Then, new homework including new questions and class-standing are written on the IC module 3 (step S75). Finally, the hybrid card 1 is returned to the student (step S76).

FIG. 18 is a flow chart showing the operation of the sub data processing apparatus 14 shown in FIGS. 2 and 3. At first the initial image I1 shown in FIG. 10A is displayed on the monitor 16f (step S81), and the apparatus is in a condition for awaiting the insertion of the hybrid card 1 (step S82). When it is judged that the hybrid card 1 is inserted into the card reader and writer 15, an input menu M6 illustrated in FIG. 19A is displayed on the monitor, and then the apparatus is in a condition for awaiting the key entry (step S84). Next it is checked whether "Display of Class-standing" is selected or not in a step S85. If this is selected, the data stored in the IC module 3 of hybrid card 1 is read out, and a graph showing the class-standing of the student is displayed on the monitor (step S86). After that, the apparatus becomes in a condition for awaiting the key operation (step S87), and it is checked whether the display of the class-standing data is finished or not (step S88).

In the step S85, if the display of the class-standing graph is not selected, then it is further checked whether "Display of Old Question and Answer" is selected or not (step S89). If this is selected, the data stored in the IC module 3 is read out, and the old questions and answers are displayed on the monitor (step S90). Then, the apparatus is in a condition for awaiting the key entry (step S91), and it is further checked whether the display of old questions and answers is finished or not (step S92). In the step S89, if the "Display of Old Question and Answer" is not selected, it is further checked whether "Display of New Question" is selected or not (step S93). If this is selected, the data stored on the IC module 3 of hybrid card 1 is read out, and a new question given for the student as homework is displayed on the monitor (step S94). Then the student enters an answer to this question by operating the keyboard 16e (step S95). This operation is repeated until all answers have been entered (step S96). After all the answers have been entered, the answers are recorded on the IC module 3 of hybrid card 1.

Figure 20:
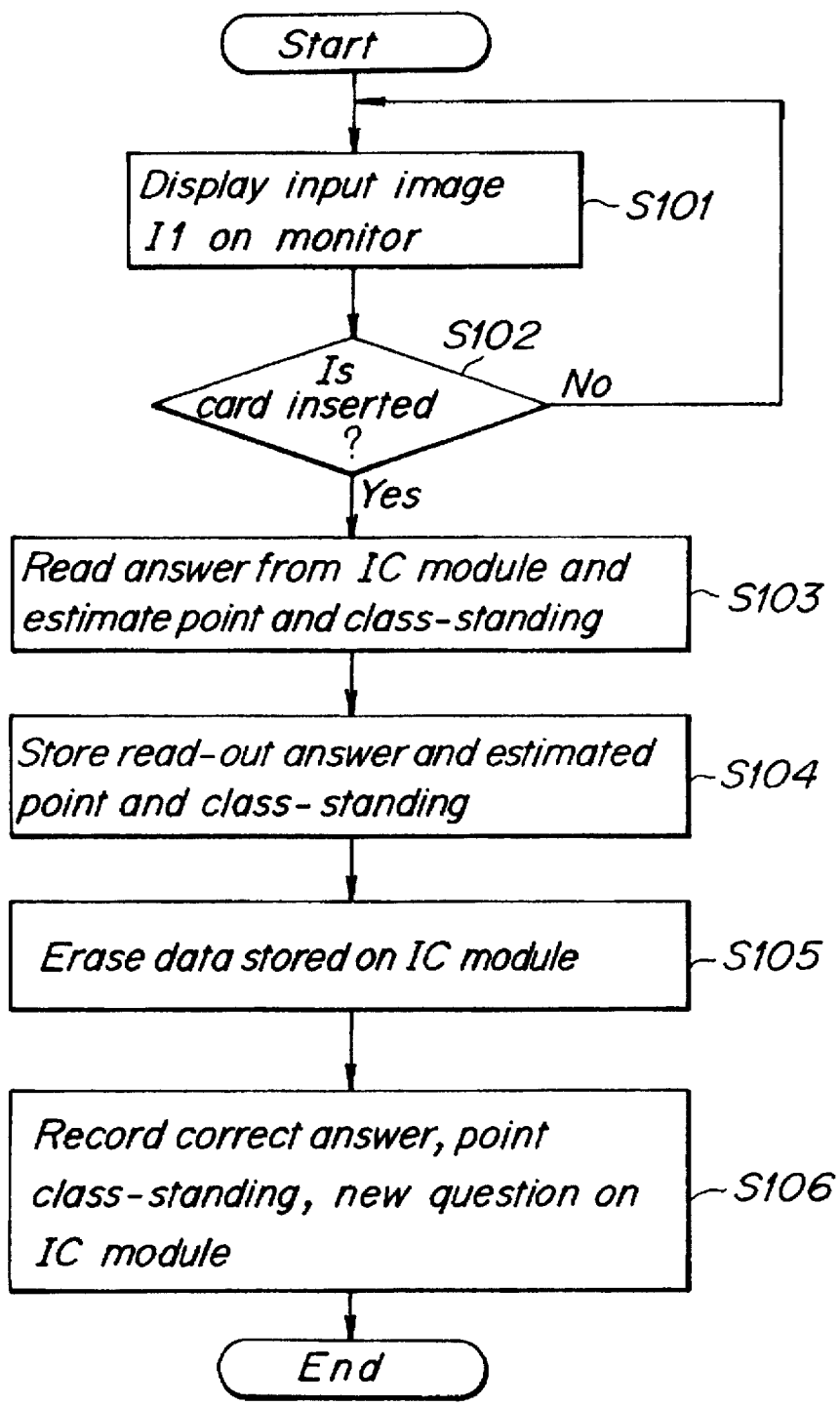
FIG. 20 is a flow chart representing the operation of the main data processing apparatus provided in the educational facility.

FIG. 20 is a flow chart representing the operation of the main data processing apparatus 11 installed in the educational facility. At first the input image I1 is displayed on the monitor 13f of the signal processing device 13 of the main data processing apparatus 11 (step S101), and the apparatus is in a condition for awaiting the insertion of the hybrid card 1 (step S102). When it is confirmed that the hybrid card 1 is inserted into the main data processing apparatus 11, the answers stored in the IC module 3 of hybrid card 1 are read out, and the read-out answers are processed by the CPU 13b such that the student's answers are compared with reference answers to estimate a point of the student (step S103). In a step S104, the thus read-cut answers and estimated point of the student are stored in the RAM 13c (step S104). Then, the data stored in the IC module 3 is erased (step S105). Finally the correct answers for the last questions, estimated point and class-standing of the student, and new questions are written on the IC module (step S106).

The above explained embodiment uses the hybrid card 1 in the system shown in FIGS. 2 and 3 for an educational application. According to the invention, the system illustrated in FIGS. 12 and 13 may be also used for the educational application. In this system, the data written on the optical stripe 2 of hybrid card 1 can be read out by the sub data processing apparatus 32, so that a much larger amount of data can be utilized by the student.

FIGS. 21 and 22 are flow charts showing the operation of the system shown in FIGS. 12 and 13 by the educational facility and student. In the present embodiment, similar steps as those of the previous embodiment are denoted by the same step numbers used in FIGS. 18 and 20, and their explanation is dispensed with.

FIG. 21 shows the flow chart representing the operation of the sub data processing apparatus 31 which can read the data not only from the IC module 3, but also from the optical stripe 2. Almost all steps are the same as those shown in FIG. 18, but in the present embodiment, in the step S86, the data is read out of the optical stripe 2 of hybrid card 1, and further in the step S94, the data is read out of the optical stripe, and a new question is displayed on the monitor. The storing capacity of the optical stripe 2 is much larger than that of the IC module 3, so that a much larger amount of data can be written on the optical stripe. Therefore, in the present embodiment, the IC module 3 is solely used to store the answers of the student.

FIG. 22 is a flow chart showing the operation of the main data processing apparatus 11 in the present embodiment. The steps S101 to S105 are entirely the same as those shown in FIG. 20, but in the step S106, the correct answers, estimated point and class-standing, and new questions are written on the optical stripe 2.

In the present embodiment, in the main data processing apparatus 11, the data is recorded only on the optical stripe 2, but it is possible to record data on the IC module 3. For instance, additional questions may be recorded on the IC module 3 in the educational facility. In such a case, these additional questions may be read out by the sub data processing apparatus, and the student may solve them. In this case, in the step S83, an input menu M7 shown in FIG. 19B may be displayed. Further, any other data useful for the student may be recorded on the IC module 3.

The present invention is not limited to the embodiments so far explained, but many modifications and alternations may be conceived by those skilled in the art within the scope of the invention. For instance, the hybrid card may be formed to include a magnetic stripe in addition to the optical stripe and IC module. Further, the information managing system according to the invention may be adapted to various applications other than the above explained medical and educational applications. For example, the system according to the invention may be used for managing personal information for a physical exercise course and personal physical data in physical training. In this case, the main data processing apparatus is installed in a gymnasium or training center.

As explained above in detail, in the information managing system according to the invention, there are provided the main data processing apparatus which can write data on both the data record area of once-write type and the data record area of rewritable type and the sub data processing apparatus which can write data only on the data record area of rewritable type; as a result, the sub data processing apparatus can be made simple in construction, small in size and cheap in cost. Further, as the sub data processing apparatus could not write data on the data record area of once-write type, there is no fear that the previously recorded data on this data record area of write-once type might be erased or altered. Moreover, the predetermined data stored on the hybrid card can be hidden from a user so that the data security function can be attained.

What is claimed is:

1. A system for managing information by using a hybrid card having a first data record area of write-once type and a second data record area of rewritable type, said system comprising:

a main data processing apparatus which comprises a first card treating means for writing and reading data on and from said first data record area and a second card treating means for writing and reading data on and from said second data record area; and a sub data processing apparatus which is arranged separately from said main data processing apparatus and which comprises a card treating means for writing and reading data on and from said second data record area.

2. A system according to claim 1, wherein said first data record area in the hybrid card comprises an optical stripe and said second data record area of rewritable type comprises an IC module, said first card treating means of the main data processing apparatus comprises an optical reading and writing unit for reading and writing data from and on said optical stripe, said second card treating means of the main data processing apparatus comprises an electrical reading and writing unit for reading and writing data from and on said IC module, and said card treating means of the sub data processing apparatus comprises an electrical reading and writing unit for reading and writing data from and on said IC module.

3. A system according to claim 1, wherein said first data record area in the hybrid card comprises an optical stripe and said second data record area of rewritable type comprises a magnetic stripe, said first card treating means of the main data processing apparatus comprises an optical reading and writing unit for reading and writing data from and on said optical stripe, said second card treating means of the main data processing apparatus comprises a magnetic reading and writing unit for reading and writing data from and on said magnetic stripe, and said card treating means of the sub data processing apparatus comprises a magnetic reading and writing unit for reading and writing data from and on said magnetic stripe.

4. A system for managing information by using a hybrid card having a first data record area of write-once type and a second data record area of rewritable type, said system comprising:

a main data processing apparatus which comprises a first card treating means for writing and reading data on and from said first data record area and a second card treating means for at least reading data from said second data record area; and a sub data processing apparatus which is arranged separately from said main data processing apparatus and which comprises a first card treating means for reading data from said first data record area and a second card treating means for at least writing data on said second data record area.

5. A system according to claim 4, wherein said first data record area in the hybrid card comprises an optical stripe and said second data record area of rewritable type comprises an IC module, said first card treating means of the main data processing apparatus comprises an optical reading and writing unit for reading and writing data from and on said optical stripe, said second card treating means of the main data processing apparatus comprises an electrical reading unit for reading data from said IC module, said first card treating means of the sub data processing apparatus comprises an optical reading unit for reading data from said optical stripe, and said second card treating means of the sub data processing apparatus comprises an electrical writing unit for writing data on said IC module.

6. A system according to claim 4, wherein said first data record area in the hybrid card comprises an optical stripe and said second data record area of rewritable type comprises an IC module, said first card treating means of the main data processing apparatus comprises an optical reading and writing unit for reading and writing data from and on said optical stripe, said second card treating means of the main data processing apparatus comprises an electrical reading and writing unit for reading and writing data from and on said IC module, said first card treating means of the sub data processing apparatus comprises an optical reading unit for reading data from said optical stripe, and said second card treating means of the sub data processing apparatus comprises an electrical reading and writing unit for reading and writing data from and on said IC module.

7. A system according to claim 5, wherein said optical reading unit of the sub data processing apparatus comprises means for reading only limited data stored in the optical stripe.

8. A system according to claim 4, wherein said first data record area in the hybrid card comprises an optical stripe and said second data record area of rewritable type comprises a magnetic stripe, said first card treating means of the main data processing apparatus comprises an optical reading and writing unit for reading and writing data from and on said optical stripe, said second card treating means of the main data processing apparatus comprises a magnetic reading and writing unit for reading and writing data from and on said magnetic stripe, said first card treating means of the sub data processing apparatus comprises an optical reading unit for reading data from said optical stripe, and said second card treating means of the sub data processing apparatus comprises a magnetic reading and writing unit for reading and writing data from and on said magnetic stripe.

9. A system according to claim 6, wherein said optical reading unit of the sub data processing apparatus comprises means for reading only limited data stored in the optical stripe.

10. A system according to claim 1, wherein said card treating means of said sub data processing apparatus comprises means for writing and reading data on and from said second data record area while said sub data processing apparatus is not in communication with said main data processing apparatus.

11. A system according to claim 1, wherein said card treating means of said sub data processing apparatus comprises means for writing and reading data on and from said second data record area while said hybrid card is removed from said main data processing apparatus.

12. A system according to claim 1, wherein said main data processing apparatus further comprises a memory which is separate from either of said first data record area and said second data record area.

13. A system according to claim 4, wherein:

said first card treating means of said sub data processing apparatus comprises means for reading data from said first data record area while said sub data processing apparatus is not in communication with said main data processing apparatus; and said second card treating means of said sub data processing apparatus comprises means for at least writing data on said second data record area while said sub data processing apparatus is not in communication with said main data processing apparatus.

14. A system according to claim 4, wherein:

said first card treating means of said sub data processing apparatus comprises means for reading data from said first data record area while said hybrid card is removed from said main data processing apparatus; and said second card treating means of said sub data processing apparatus comprises means for at least writing data on said second data record area while said hybrid card is removed from said main data processing apparatus.

15. A system according to claim 4, wherein said main data processing apparatus further comprises a memory which is separate from either of said first data record area and said second data record area.

* * * * *